(12) United States Patent
Hong et al.

(10) Patent No.: US 8,420,353 B2
(45) Date of Patent: Apr. 16, 2013

(54) HUMANIZED ANTIBODY AND PROCESS FOR PREPARING SAME

(75) Inventors: Hyo Jeong Hong, Daejeon (KR); Cheol-Young Maeng, Daejeon (KR); Gi-Hyeok Yang, Cheonan-si (KR); Meong Hee Jang, Daejeon (KR); Mee Sook Oh, Daejeon (KR); Jin-Soo Song, Daejeon (KR); Young Kug Jang, Daejeon (KR)

(73) Assignee: Aprogen, Inc. (KR)

( * ) Notice: Subject to any disclaimer, the term of this patent is extended or adjusted under 35 U.S.C. 154(b) by 1004 days.

(21) Appl. No.: 10/508,759

(22) PCT Filed: Mar. 22, 2003

(86) PCT No.: PCT/KR03/00564
§ 371 (c)(1),
(2), (4) Date: Sep. 22, 2004

(87) PCT Pub. No.: WO03/080672
PCT Pub. Date: Oct. 2, 2003

(65) Prior Publication Data
US 2007/0021595 A1    Jan. 25, 2007

(30) Foreign Application Priority Data
Mar. 22, 2002    (KR) .................. 10-2002-0015708

(51) Int. Cl.
*A61K 39/395*    (2006.01)
*C07K 16/00*    (2006.01)

(52) U.S. Cl.
USPC .............. 435/70.21; 424/130.1; 530/387.1

(58) Field of Classification Search ............... None
See application file for complete search history.

(56) References Cited

U.S. PATENT DOCUMENTS 6,020,167 A  *  2/2000  Thoma ................. 435/69.3
7,115,723 B1 * 10/2006  Hong et al. .............. 536/23.1

FOREIGN PATENT DOCUMENTS

| KR | 1999-008649 | 2/1999 |
| KR | 1999-008650 | 2/1999 |
| KR | 2000-0033008 | 6/2000 |
| WO | 97/47654 | 12/1997 |
| WO | WO 00/31141 | 6/2000 |

OTHER PUBLICATIONS

Tamura et al., Journal of Immunology, 2000, vol. 164, p. 1432-1441.*
Leong et al. Cytokine, Nov. 2001, vol. 16, p. 106-119.*
Maeng et al. Virology, 2000, vol. 270, p. 9-16.*
Kashmiri et al. (Critical Reviews in Oncology/Hematology, 2001, vol. 38, p. 3-16 in IDS on Jan. 20, 2010).*
Owens et al. (The Genetic engineering of monoclonal antibodies Journal of Immunological methods, 1994, vol. 168, p. 149-165).*
"Structural Correlates of an Anticarcinoma Antibody: Identification of Specificity-Determining Residues (SDRs) and Development of a Minimally Immunogenic Antibody Variant by Retention of SDRs Only", Midori Tamura, et al., The Journal of Immunology, vol. 164, pp. 1432-1441.
Tomoyuki Nakatani et al., Humanization of mouse anti-human IL-2 receptor antibody B-B10; Protein Engineering vol. 7 No. 3 pp. 435-443, 1994.
S. Stephens et al., Comprehensive pharmacokinetics of a humanized antibody and analysis of residual anti-idiotypic responses; Immunology 85 pp. 668-674, 1995.
Ian M. Tomlinsoin, et al., The repertoire of human germline VH sequences reveals about fifty groups of VH segments with different hypervariable loops; J. Mol. Biol. 227, pp. 776-798, 1992.
Jeffrey V. Ravetch, et al., Structure of the human immunoglobulin u locus: characterization of embryonic and rearranged J and G genes; Cell, vol. 27, pp. 583-591, Dec. 1981 (Part 2).
Jonathan P.L. Cox, et al., A directory of human germ-line VH segments reveals a strong bias in their usage; Eur. J. Immunol., 24, pp. 827-836, 1994.
Makoto Iwahashi, et al., CDR substitutions of a humanized monoclonal antibody (CC49): contributions of individual CDRs to antigen binding and immunogenicity; Molecular Immunology, 36, pp. 1079-1091, 1999.
Eduardo A. Padlan, et al., Identification of specificity-determining residues in antibodies; The FASEB Journal, vol. 9, pp. 133-139, Jan. 1995.
Chun Jeih Ryu, et al., Cloning and sequence analysis of cDNAs encoding the heavy and light chain variable regions of a human monoclonal antibody with specificity for hepatitis B surface antigen; Biochimica et Biophysica Acta, 1380, pp. 151-155, 1998.
Chun Jeih Ryu, et al., A humanized antibody with specificity for hepatitis B surface antigen; Hum. Antibod. Hybridomas, vol. 7, 3, pp. 113-122, 1996.
S.V.S. Kashmiri, et al., Development of a minimally immunogenic variant of humanized anti-carcinoma monoclonal antibody CC49; Critical Reviews in Oncology/Hematology, 38, pp. 3-16, 2001.
Stuart Rudikoff, et al., Single amino acid substitution altering antigen-binding specificity; Proc. Natl. Acad. Sci. USA, vol. 79, pp. 1979-1983, Mar. 1982, Immunology.
Muller et al., "VEGF and the Fab fragment of a humanized neutralizing antibody: crystal structure of the complex at 2.4 A resolution and mutational analysis of the interface", Structure, Current Biology Ltd., Philadelphia, PA, US, vol. 6, No. 9, Sep. 15, 1998, pp. 1153-1167.

* cited by examiner

*Primary Examiner* — Agnieszka Boesen
(74) *Attorney, Agent, or Firm* — Baker & Hostetler LLP

(57) ABSTRACT

A humanized antibody is produced by process comprising the steps of: (a) selecting a specificity determining residue (SDR) of the complementarity determining region (CDR) of murine monoclonal antibody heavy chain and light chain variable regions; and (b) grafting said SDR to at least one of the corresponding amino acid sequences in human antibody variable regions.

7 Claims, 10 Drawing Sheets

FIG. 2A

```
              (SEQ ID NO. 28)   Q   V   Q   L   Q   Q   S   G   P   E   L   V   K   P
KRI27VH       (SEQ ID NO. 27)   CAG GTC CAG CTG CAG CAG TCT GGA CCT GAA CTG GTG AAG CCT  42
              (SEQ ID NO. 44)   Q   V   Q   L   V   Q   S   G   A   E   V   K   K   P
DP7-JH4       (SEQ ID NO. 43)   CAG GTG CAG CTG GTG CAG TCT GGG GCT GAG GTG AAG AAG CCT
HZI           (SEQ ID NO. 35)   CAG GTC CAG CTG GTG CAG TCT GGA GCT GAA GTG GTG AAG CCT
HZVII         (SEQ ID NO. 1)    CAG GTC CAG CTG GTG CAG TCT GGA GCT GAA GTG AAG AAG CCT
HZI           (SEQ ID NO. 36)   -   -   -   -   V   -   -   A   -   V   -   -   -   -
HZVII         (SEQ ID NO. 2)    -   -   -   -   V   -   -   A   -   V   K   -   -   -

(SEQ ID NO. 28)   G   A   S   V   K   I   S   C   K   A   S   G   Y   A
KRI27VH       (SEQ ID NO. 27)   GGG GCC TCA GTG AAG ATT TCC TGC AAA GCT TCT GGC TAC GCA  84
              (SEQ ID NO. 44)   G   A   S   V   K   V   S   C   K   A   S   G   Y   T
DP7-JH4       (SEQ ID NO. 43)   GGG GCC TCA GTG AAG GTT TCC TCC AAG GCA TCT GGA TAC ACC
HZI           (SEQ ID NO. 35)   GGG GCC TCA GTG AAG GTT TCC TGC AAA GCT TCT GGC TAC GCA
HZVII         (SEQ ID NO. 1)    GGG GCC TCA GTG AAG GTT TCC TGC AAA GCT TCT GGC TAC ACC
HZI           (SEQ ID NO. 36)   -   -   -   -   -   V   -   -   -   -   -   -   -   -
HZVII         (SEQ ID NO. 2)    -   -   -   -   -   V   -   -   -   -   -   -   -   T

CDR1
              (SEQ ID NO. 28)   P   S   S   S   W   M   N   W   V   K   Q   R   P   G
KRI27VH       (SEQ ID NO. 27)   TTC AGT AGT TCT TGG ATG AAC TGG GTG AAG CAG AGG CCT GGA  126
              (SEQ ID NO. 44)   F   T   S   Y   Y   M   H   W   V   R   Q   A   P   G
DP7-JH4       (SEQ ID NO. 43)   TTC ACC AGC TAC TAT ATG CAC TGG GTG CGA CAG GCC CCT GGA
HZI           (SEQ ID NO. 35)   TTC AGT AGT TCT TGG ATG AAC TGG GTG CGA CAG GCC CCT GGA
HZVII         (SEQ ID NO. 1)    TTC ACC AGT GCT TGG ATG AAC TGG GTG CGA CAG GCC CCT GGA
HZI           (SEQ ID NO. 36)   -   -   -   -   -   -   -   -   -   -   R   -   A   -
HZVII         (SEQ ID NO. 2)    -   T   -   A   -   -   -   -   -   -   R   -   A   -

CDR2
              (SEQ ID NO. 28)   Q   G   L   E   W   I   G   R   I   Y   P   G   D   G
KRI27VH       (SEQ ID NO. 27)   CAG GGT CTT GAG TGG ATT GGA CGG ATT TAT CCT GGA GAT GGA  168
              (SEQ ID NO. 44)   Q   G   L   E   W   M   G   I   I   N   P   S   G   G
DP7-JH4       (SEQ ID NO. 43)   CAA GGG CTT GAG TGG ATG GGA ATA ATC AAC CCT AGT GGT GGT
HZI           (SEQ ID NO. 35)   CAG GGT CTT GAG TGG ATT GGA CGG ATT TAT CCT GGA GAT GGA
HZVII         (SEQ ID NO. 1)    CAG GGT CTT GAG TGG ATG GGA CGG ATT TAT CCT AGT GGT GGA
HZI           (SEQ ID NO. 36)   -   -   -   -   -   -   -   -   -   -   -   -   -   -
HZVII         (SEQ ID NO. 2)    -   -   -   -   -   M   -   -   -   -   -   S   G   -
```

FIG. 2B

|  |  | CDR2 |
|---|---|---|
| (SEQ ID NO. 28) | | D T N Y N G K F K G K A T L |
| KRI27VH (SEQ ID NO. 27) | | GAT ACT AAC TAC AAT GGG AAG TTC AAG GGC AAG GCC ACA CTG 210 |
| (SEQ ID NO. 44) | | S T S Y A Q K F Q G R V T M |
| DP7-JH4 (SEQ ID NO. 43) | | AGC ACA AGC TAC GCA CAG AAG TTC CAG GGC AGA GTC ACC ATG |
| HZI (SEQ ID NO. 35) | | GAT ACT AAC TAC GCA CAG AAG TTC CAG GGC AAG GCC ACA CTG |
| HZVII (SEQ ID NO. 1) | | AGC ACT AGC TAC GCA CAG AAG TTC CAG GGC AGA GTC ACA ATG |
| HZI (SEQ ID NO. 36) | | — — — — A Q — — Q — — — — — |
| HZVII (SEQ ID NO. 2) | | S — S — A Q — — Q — R V — M |

| (SEQ ID NO. 28) | | T A D K S S S T A Y M Q L S |
| KRI27VH (SEQ ID NO. 27) | | ACT GCA GAC AAA TCC TCC AGC ACA GCC TAC ATG CAG CTC AGC 252 |
| (SEQ ID NO. 44) | | T R D T S T S T V Y M E L S |
| DP7-JH4 (SEQ ID NO. 43) | | ACC AGG GAC ACG TCC ACG AGC ACA GTC TAC ATG GAG CTG AGC |
| HZI (SEQ ID NO. 35) | | ACT GCA GAC AAA TCC ACG AGC ACA GCC TAC ATG GAG CTC AGC |
| HZVII (SEQ ID NO. 1) | | ACT GCA GAC AAA TCC ACG AGC ACA GTC TAC ATG GAG CTC AGC |
| HZI (SEQ ID NO. 36) | | — — — — — T — — — — — E — — |
| HZVII (SEQ ID NO. 2) | | — — — — — T — — V — — E — — |

| (SEQ ID NO. 28) | | S L T S V D S A V Y F C A R |
| KRI27VH (SEQ ID NO. 27) | | AGC CTG ACC TCT GTG GAC TCT GCG GTC TAT TTC TGT GCA AGA 294 |
| (SEQ ID NO. 44) | | S L R S E D T A V Y Y C A R |
| DP7-JH4 (SEQ ID NO. 43) | | AGC CTG AGA TCT GAG GAC ACG GCC GTG TAT TAC TGT GCG AGA |
| HZI (SEQ ID NO. 35) | | AGC CTG AGA TCT GAG GAC ACG GCG GTC TAT TTC TGT GCA AGA |
| HZVII (SEQ ID NO. 1) | | AGC CTG AGA TCT GAG GAC ACG GCG GTG TAT TAC TGT GCA AGA |
| HZI (SEQ ID NO. 36) | | — — R — E — T — — — — — — — |
| HZVII (SEQ ID NO. 2) | | — — R — E — T — — — Y — — — |

|  |  | CDR3 |
|---|---|---|
| (SEQ ID NO. 28) | | E Y D E A Y W G Q G T L V T |
| KRI27VH (SEQ ID NO. 27) | | GAG TAC GAC GAG GCT TAC TGG GGC CAA GGG ACT CTG GTC ACT 336 |
| (SEQ ID NO. 44) | | W G Q G T L V T |
| DP7-JH4 (SEQ ID NO. 43) | | NNN NNN NNN NNN NNN TAC TGG GGC CAA GGA ACT CTG GTC ACT |
| HZI (SEQ ID NO. 35) | | GAG TAC GAC GAG GCT TAC TGG GGC CAA GGA ACT CTG GTC ACT |
| HZVII (SEQ ID NO. 1) | | GAG TAC CGG GTT GCC CGT TGG GGC CAA GGA ACT CTG GTC ACT |
| HZI (SEQ ID NO. 36) | | — — — — — — — — — — — — — — |
| HZVII (SEQ ID NO. 2) | | — — R V — R — — — — — — — — |

FIG. 2C

|         |               |     |     |     |     |
|---------|---------------|-----|-----|-----|-----|
|         | (SEQ ID NO. 28) | V   | S   | A   |     |
| KRI27VH | (SEQ ID NO. 27) | GTC | TCT | GCA | 345 |
|         | (SEQ ID NO. 44) | V   | S   | S   |     |
| DP7-JH4 | (SEQ ID NO. 43) | GTC | TCT | TCA |     |
| HZI     | (SEQ ID NO. 35) | GTC | TCT | TCA |     |
| HZVII   | (SEQ ID NO. 1)  | GTC | TCT | TCA |     |
| HZI     | (SEQ ID NO. 36) | —   | S   |     |     |
| HZVII   | (SEQ ID NO. 2)  | —   | S   |     |     |

FIG. 3
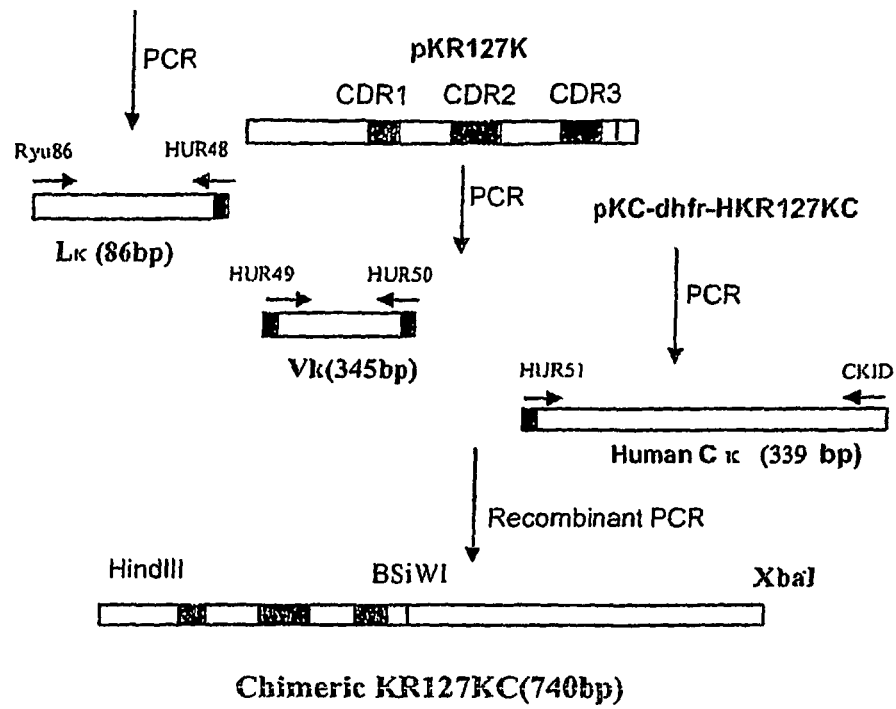
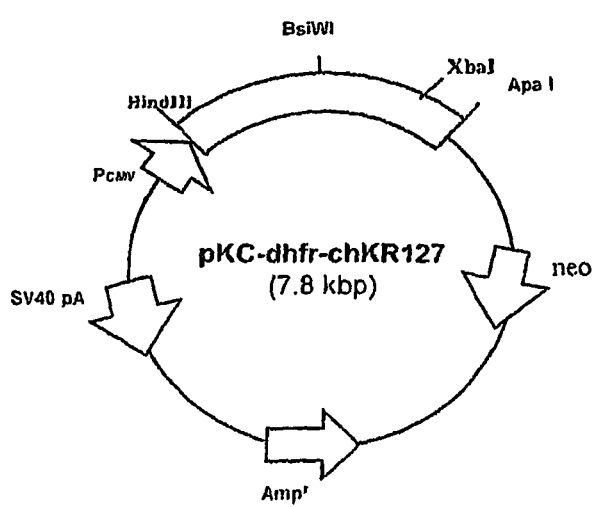

FIG. 4A

```
              (SEQ ID NO. 30)    D   I   L   M   T   Q   T   P   L   I   L   S   V   T
KRI27VK       (SEQ ID NO. 29)    GAT ATC TTG ATG ACC CAA ACT CCA CTT ATT TTG TCG GTT ACC 42
              (SEQ ID NO. 46)    D   I   V   M   T   Q   T   P   L   S   L   S   V   T
DPK12-JK4     (SEQ ID NO. 45)    GAT ATT GTG ATG ACC CAG ACT CCA CTC TCT CTG TCC GTC ACC
HZI           (SEQ ID NO. 37)    GAT ATC TTG ATG ACC CAA ACT CCA CTT TCT TTG TCG GTT ACC
HZIV          (SEQ ID NO. 3)     GAT ATC GTG ATG ACC CAA ACT CCA CTT TCT TTG TCG GTT ACC
HZI           (SEQ ID NO. 38)    -   -   -   -   -   -   -   -   -   S   -   -   -   -
HZIV          (SEQ ID NO. 4)     -   -   V   -   -   -   -   -   -   S   -   -   -   -

CDR1
              (SEQ ID NO. 30)    I   G   Q   P   A   S   I   S   C   K   S   S   Q   S
KRI27VK       (SEQ ID NO. 29)    ATT GGA CAA CCA GCC TCT ATC TCT TGC AAG TCA AGT CAG AGC 84
              (SEQ ID NO. 46)    P   G   Q   P   A   S   I   S   C   K   S   S   Q
DPK12-JK4     (SEQ ID NO. 45)    CCT GGA CAG CCG GCC TCC ATC TCC TGC AAG TCT AGT CAG AGC
HZI           (SEQ ID NO. 37)    CCT GGA CAA CCA GCC TCT ATC TCT TGC AAG TCA AGT CAG AGC
HZIV          (SEQ ID NO. 3)     CCT GGA CAA CCA GCC TCT ATC TCT TGC AAG TCA AGT CAG AGC
HZI           (SEQ ID NO. 38)    P   -   -   -   -   -   -   -   -   -   -   -   -   -
HZIV          (SEQ ID NO. 4)     P   -   -   -   -   -   -   -   -   -   -   -   -   -

CDR1
              (SEQ ID NO. 30)    L   L   Y   S   N   G   K   T   Y   L   N   W   L   L
KRI27VK       (SEQ ID NO. 29)    CTC TTA TAT AGT AAT GGA AAA ACC TAT TTG AAT TGG TTA TTA 126
              (SEQ ID NO. 46)    L   L   H   S   D   G   K   T   Y   L   Y   W   Y   L
DPK12-JK4     (SEQ ID NO. 45)    CTC CTG CAT AGT GAT GGA AAG ACC TAT TTG TAT TGG TAC CTG
HZI           (SEQ ID NO. 37)    CTC TTA TAT AGT AAT GGA AAA ACC TAT TTG AAT TGG TTA TTA
HZIV          (SEQ ID NO. 3)     CTC TTA TAT AGT AAT GGA AAA ACC TAT TTG AAT TGG TTA TTA
HZI           (SEQ ID NO. 38)    -   -   -   -   -   -   -   -   -   -   -   -   -   -
HZIV          (SEQ ID NO. 4)     -   -   -   -   -   -   -   -   -   -   -   -   -   -

CDR2
              (SEQ ID NO. 30)    Q   R   P   G   Q   S   P   K   R   L   I   Y   L   V
KRI27VK       (SEQ ID NO. 29)    CAG AGG CCA GGC CAG TCT CCA AAG CGC CTA ATC TAT CTG GTG 168
              (SEQ ID NO. 46)    Q   K   P   G   Q   P   P   Q   L   L   I   Y   E   V
DPK12-JK4     (SEQ ID NO. 45)    CAG AAG CCA GGC CAG CCT CCA CAG CTC CTG ATC TAT GAA GTT
HZI           (SEQ ID NO. 37)    CAG AAG CCA GGC CAG TCT CCA AAG CGC CTA ATC TAT CTG GTG
HZIV          (SEQ ID NO. 3)     CAG AAG CCA GGC CAG CCT CCA CAG CGC CTA ATC TAT CTG GTG
HZI           (SEQ ID NO. 38)    -   K   -   -   -   -   -   -   -   -   -   -   -   -
HZIV          (SEQ ID NO. 4)     -   K   -   -   -   P   -   Q   -   -   -   -   -   -
```

FIG. 4B

```
                              CDR2
              (SEQ ID NO. 30)    S   K   L   D   S   G   V   P   D   R   F   T   G   S
KRI27VK       (SEQ ID NO. 29)   TCT AAA CTG GAC TCT GGA GTC CCT GAC AGG TTC ACT GGC AGT 210
              (SEQ ID NO. 46)    S   N   R   F   S   G   V   P   D   R   F   S   G   S
DPK12-JK4     (SEQ ID NO. 45)   TCC AAC CGG TTC TCT GGA GTG CCA GAT AGG TTC AGT GGC AGC
HZI           (SEQ ID NO. 37)   TCT AAA CTG GAC TCT GGA GTC CCT GAC AGG TTC AGT GGC AGT
HZIV          (SEQ ID NO. 3)    TCT AAT CGG GAC TCT GGA GTC CCT GAC AGG TTC AGT GGC AGT
HZI           (SEQ ID NO. 38)    -   -   -   -   -   -   -   -   -   -   -   S   -   -
HZIV          (SEQ ID NO. 4)     -   N   R   -   -   -   -   -   -   -   -   S   -   -

(SEQ ID NO. 30)    G   S   G   T   D   F   T   L   K   I   I   R   V   E
KRI27VK       (SEQ ID NO. 29)   GGA TCA GGA ACA GAT TTT ACA CTG AAA ATC ATC AGA GTG GAG 252
              (SEQ ID NO. 46)    G   S   G   T   D   F   T   L   K   I   S   R   V   E
DPK12-JK4     (SEQ ID NO. 45)   GGG TCA GGG ACA GAT TTC ACA CTG AAA ATC AGC CGG GTG GAG
HZI           (SEQ ID NO. 37)   GGA TCA GGA ACA GAT TTT ACA CTG AAA ATC AGC AGA GTG GAG
HZIV          (SEQ ID NO. 3)    GGA TCA GGA ACA GAT TTT ACA CTG AAA ATC AGC AGA GTG GAG
HZI           (SEQ ID NO. 38)    -   -   -   -   -   -   -   -   -   -   S   -   -   -
HZIV          (SEQ ID NO. 4)     -   -   -   -   -   -   -   -   -   -   S   -   -   -

CDR3
              (SEQ ID NO. 30)    A   E   D   L   G   V   Y   Y   C   V   Q   G   T   H
KRI27VK       (SEQ ID NO. 29)   GCT GAG GAT TTG GGA GTT TAT TAC TGC GTG CAA GGT ACA CAT 294
              (SEQ ID NO. 46)    A   E   D   V   G   V   Y   Y   C   M   Q   S   I   Q
DPK12-JK4     (SEQ ID NO. 45)   GCT GAG GAT GTT GGG GTT TAT TAC TGC ATG CAA AGT ATA CAG
HZI           (SEQ ID NO. 37)   GCT GAG GAT GTT GGA GTT TAT TAC TGC GTG CAA GGT ACA CAT
HZIV          (SEQ ID NO. 3)    GCT GAG GAT GTT GGA GTT TAT TAC TGC GTG CAA GGT ACA CAT
HZI           (SEQ ID NO. 38)    -   -   -   V   -   -   -   -   -   -   -   -   -   -
HZIV          (SEQ ID NO. 4)     -   -   -   V   -   -   -   -   -   -   -   -   -   -

CDR3
              (SEQ ID NO. 30)    F   P   Q   T   F   G   G   T   K   L   E   I   K
KRI27VK       (SEQ ID NO. 29)   TTT CCT CAG ACG TTC GGT GGA GGG ACC AAG CTG GAA ATC AAA 336
              (SEQ ID NO. 46)    L   P       T   F   G   G   T   K   V   E   I   K
DPK12-JK4     (SEQ ID NO. 45)   CTT CCT CCN ACG TTC GGT GGA GGC ACC AAG GTG GAA ATC AAA
HZI           (SEQ ID NO. 37)   TTT CCT CAG ACG TTC GGT GGA GGC ACC AAG GTG GAA ATC AAA
HZIV          (SEQ ID NO. 3)    TTT CCT CAG ACG TTC GGT GGA GGC ACC AAG GTG GAA ATC AAA
HZI           (SEQ ID NO. 38)    -   -   -   -   -   -   -   -   -   V   -   -   -
HZIV          (SEQ ID NO. 4)     -   -   -   -   -   -   -   -   -   V   -   -   -
```

HUMANIZED ANTIBODY AND PROCESS FOR PREPARING SAME

FIELD OF THE INVENTION

The present invention relates to a process for preparing a humanized antibody by grafting SDRs (specificity determining residues) in CDRs (complementary determining residues) of murine monoclonal antibody to human antibody and the humanized antibody prepared according to said process.

BACKGROUND OF THE INVENTION

For preventing infectious diseases such as hepatitis B, there has generally been used a method of administering immunoglobulins formed in blood plasma against a target antigen. However, the method has the problems that the immunoglobulins generally have low specificity and may contain contaminants.

Murine monoclonal antibody derived from mouse has been reported to have high affinity to antigen and is suitable for mass-production. However, repeated injection of murine monoclonal antibody induces an immune response because the murine antibody is regarded as a foreign antigen in humans (Shawler D. L. et al., *J. Immunol.*, 135, 1530-1535 (1985)).

Accordingly, numerous efforts have been made to generate "humanized antibody" by: grafting the CDR (complementarity determining region) of murine monoclonal antibody variable region which directly binds to antigens, to a human antibody framwork (CDR-grafting method); and replacing the amino acid residues of the human antibody framework region (FR) that influence the CDR conformation with the amino acid residues of murine monoclonal antibody. The humanized antibody thus obtained maintains the affinity and specificity of original murine monoclonal antibody, and minimizes HAMA(human anti-mouse antibody) response in humans (Riechmann et al., *Nature*, 332, 323-327(1988); Queen C. et al., *Proc. Natl. Acad. Sci. USA*, 86, 10029-10033 (1989); Nakatani et al., *Protein Engineering*, 7, 435-443 (1994)). However, this humanized antibody still causes problems when injected repeatedly into humans (Stephens et al., *Immunology*, 85, 668-674(1995); Sharkey et al., *Cancer Research*, 55, 5935s-5945s(1995)).

Approximately 300 millions of world population carry hepatitis B virus ("HBV") which may cause chronic infection, leading to cirrhosis and hepatocellular carcinoma (Tiollais P. and Buendia M. A., *Sci. Am.*, 264, 48(1991)). The HBV envelope consists of three proteins, major protein containing S antigen, middle protein containing S and pre-S2 antigens, and large protein containing S, pre-S2 and pre-S1 antigens (Neurath A. R. and Kent S. B., *Adv. Vir. Res.*, 34, 65-142 (1988)). These surface antigens have been known to play important roles in the process of forming antibodies against HBV in hepatitis patient. The pre-S1 region, in particular, is found on infectious viral particles (Heermann et al., *J. Virol.*, 52, 396-402(1984)) and plays a role in attachment to cell surface infection (Neurath et al., *Cell*, 46, 429(1986); Pontisso et al., *Virol.*, 173, 533, (1989); Neurath et al., *Vaccine*, 7, 234(1989)). Thus a monoclonal antibody against the pre-S1 would be effective against viral infection.

The present inventors have previously reported a murine monoclonal antibody (KR127) against HBV pre-S1 (Korean Patent No. 246128), a murine monoclonal antibody KR127 gene encoding same (Korean Patent No. 250832) and a humanized antibody (HZKP127I) of KR127 prepared by CDR-grafting method (Korean Patent No. 246128).

The present inventors have further endeavored to develop a humanized antibody having minimized adverse immune response (HAMA response) as well as enhanced affinity to antigen, and found that HAMA response can be reduced when the amino acid residues of CDR of mouse antibody are replaced with those of human antibody.

SUMMARY OF THE INVENTION

Accordingly, it is an object of the present invention to provide a process for preparing a humanized antibody which is expected to show lower HAMA response and has higher affinity than humanized antibody of the prior art.

It is another object of the present invention to provide a humanized antibody prepared according to said process.

It is a further another object of the present invention to provide a DNA encoding the heavy chain or light chain of said antibody and a vector comprising said DNA.

It is a still further object of the present invention to provide a microorganism transformed with said vector.

In accordance with one aspect of the present invention, there is provided a process for preparing a humanized antibody comprising the steps of: (a) selecting a specificity determining residue (SDR) of the complementarity determining region (CDR) of murine monoclonal antibody heavy chain and light chain variable regions; and (b) grafting the amino acid residues of said SDR to at least one of the corresponding amino acid sequences in human antibody variable regions.

BRIEF DESCRIPTION OF THE DRAWINGS

The above and other objects and features of the present invention will become apparent from the following description of the invention taken in conjunction with the following accompanying drawings; which respectively show:

FIG. 2: the nucleotide and amino acid sequence of the humanized heavy chain variable region;

FIG. 3: the procedure for constructing an expression vector of a chimeric light chain;

FIG. 4: the nucleotide and amino acid sequence of the humanized light chain variable region;

DETAILED DESCRIPTION OF THE INVENTION

Figure 1:
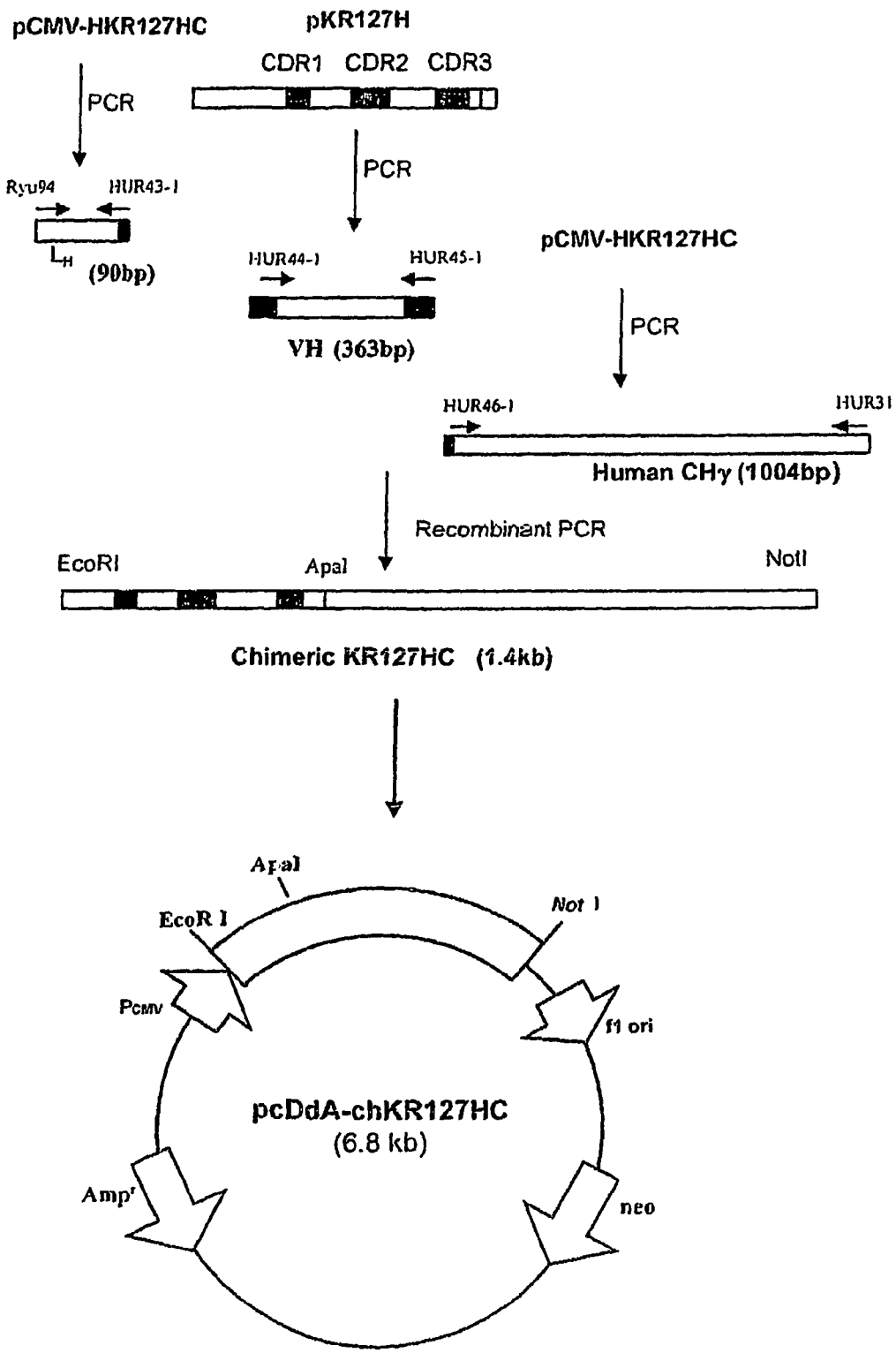
FIG. 1: the procedure for constructing an expression vector of a chimeric heavy chain.

The humanized antibody of the present invention may be prepared by grafting the amino acid residues of SDR of murine monoclonal antibody to the corresponding amino acid sequences in human antibody variable regions.

SDRs of the murine monoclonal antibody used in the present invention may be determined by independently replacing each amino acid residue of CDR of the murine monoclonal antibody with alanine, selecting transformants which have lower affinity ($k_D$) to antigen than the original murine antibody and determining the replaced CDR amino acid residues of said transformants as SDRs.

Further, in order to enhance the affinity to antigen, the CDR residues of a mouse antibody that increase the affinity and the framework residues that influence the conformation of CDR loops may also be grafted to the corresponding sites of human antibody.

For example, the present invention describes a process for preparing a humanized antibody for hepatitis B virus (HBV) pre-S1 by using murine monoclonal antibody KR127 (Korean Patent No. 250832) as follows:

After selecting SDR amino acid residues, which play important roles in binding with antigen, from CDR of the murine monoclonal antibody KR127 heavy and light chains, chimeric heavy chain and chimeric light chain genes may be prepared by combining either the variable region of KR127 antibody heavy chain with the constant region ($C_\gamma$ 1) of human antibody or the variable region of KR127 antibody light chain with the constant region ($C_\kappa$) of human antibody.

SDRs of the murine monoclonal antibody for HBV pre-S1 are determined by replacing each amino acid residue of CDR HCDR1 (aa 31-35), HCDR2 (aa 50-65) and HCDR3 (aa 95-102) of the heavy chain (SEQ ID NO: 2) and CDR LCDR1 (aa 24-34), LCDR2(aa 50-56) and LCDR3(aa 89-97) of the light chain (SEQ ID NO: 4) of the murine monoclonal antibody KR127 with alanine according to the alanine scanning mutagenesis method and selecting the amino acid residues (SDRs) whose replacement with alanine bring about more than 3 times reduction in the affinity to antigen ($K_D$) as compared with the original murine antibody. Throughout this description, amino acid residue number is assigned according to Kabat numbering scheme (Kabat, E. A. et al, Sequences of Proteins of Immunological Interest. *National Institute of Health*, Bethesda, Md., 1991).

Examples of preferred SDR include tryptophan at position 33 (it is represented as "Trp33"), Met34, and Asn35 of HCDR1; Arg50, Tyr52, and Pro52a of HCDR2; Glu95, Tyr96, and Glu98 of HCDR3 of the murine monoclonal antibody KR27 heavy chain; Leu27b, Tyr27d, Ser27e; Asn28, Lys30, Tyr32, and Asn34 of LCDR1; Leu50 and Asp55 of LCDR2; and Val89, Gln90, Gly91, Thr92, His93, Phe94, Pro95, and Gln96 of LCDR3 of the murine monoclonal antibody KR127 light chain.

The humanized antibody of the present invention can be prepared by grafting one or more SDRs determined as above onto the human antibody. heavy chain and/or light chain. The human antibody heavy chain which may be used in the present invention is human heavy chain DP7-JH4 consisting of human immunoglobulin germline VH gene segment DP7 (Tomlinson et al., J. Mol. Biol., 227, 776-798, 1992) and JH4 segment (Ravetch et al., Cell, 27, 583-591, 1981). The human antibody light chain which may be used in the present invention is human light chain DPK12-JK4 consisting of human immunoglobulin germline VK gene segment DPK12 (Cox et al., Eur. J. Immunol., 24, 827-836 (1994)) and JH4 segment (Hieter et al., J. Biol. Chem., 257, 1516-1522 (1982)).

The humanized heavy chain of the present invention may be prepared by grafting at least one of Trp33, Met34, and Asn35 of HCDR1; Arg50, Tyr52, and Pro52a of HCDR2; Glu95, Tyr96, and Glu98 of HCDR3 of the murine monoclonal antibody KR127 heavy chain to the corresponding amino acid sequences in human antibody heavy chain. The inventive humanized light chain may be prepared by grafting at least one of Leu27b, Tyr27d, Ser27e; Asn28, Lys30, Tyr32, and Asn34 of LCDR1; Leu50 and Asp55 of LCDR2; and Val89, Gln90, Gly91, Thr92, His93, Phe94, Pro95, and Gln96 of LCDR3 of the murine monoclonal antibody KR127 light chain to the corresponding amino acid sequences in human antibody light chain DPH12-JK4.

Moreover, the affinity to antigen of the humanized antibody can be enhanced by the follow substitutions:

(a) the amino acid residue at position 32 in HCDR1 of the modified human heavy chain DP7-JH4 by Ala;

(b) the amino acid residue at position 97 in HCDR3 of the modified human heavy chain DP7-JH4 by Arg or Ala;

(c) the amino acid residue at position98 in HCDR3 of the modified human heavy chain DP7-JH4 by Val; and (d) the amino acid residue at position 102 in HCDR3 of the modified human heavy chain DP7-JH4 by Arg or Ala.

In addition, A1a71 and Lys73 in framework region 3 in the heavy chain variable region of KR127, which affects the conformation of the CDR loop, may further be grafted to human heavy chain DP7-3H4. Also, Leu36 and Arg46 in framework region 2 in the light chain variable region of KR127, which affects conformation of CDR loop, may be further grafted to human light chain DPK12-JK4.

The heavy chain variable region of humanized antibody of the present invention has the amino acid sequence of SEQ ID NO: 2, preferably encoded by the nucleotide sequence of SEQ ID NO: 1 and the inventive light chain variable region of humanized antibody has the amino acid sequence of SEQ ID NO: 4, preferably encoded by the nucleotide sequence of SEQ ID NO: 3.

The humanized antibody heavy chain and light chain of the present invention may be encoded by a gene comprising a nucleotide sequence deduced from the humanized antibody heavy chain and light chain according to the genetic code. It is known that several different codons encoding a specific amino acid may exist due to the codon degeneracy, and, therefore, the present invention includes in its scope all nucleotide sequences deduced from the humanized antibody heavy chain and light chain amino acid sequence. Preferably, the humanized antibody heavy chain and light chain gene sequences include one or more preferred codons of host cell.

The humanized antibody consisted of the humanized heavy chain HuKR127HC of the present invention and humanized light chain HZKR127I prepared by CDR-grafting has an affinity to antigen of about over 50 times higher than that of the humanized antibody HZKR127I.

The humanized antibody consisting of the humanized heavy chain HuKR127KC of the present invention and humanized light chain HZKR127I prepared by CDR-grafting has an affinity to antigen equal to that of the humanized antibody HZKR127I.

The hybridoma cell line KKCTC1019BP corresponds to the pHmKR127HC vector and the hybridoma cell line KCTC10199BP corresponds to the PHuKR127KC vector. A scientific description of each microorganism was deposited pursuant to the Budapest Treaty and contains the following information:

1. Depository:
   Korea Research Institute of Bioscience and biotechnology (KRIBB), #52 Oun-dong, Yusong-Ku, Taiion, 305-333, Republic of Korea.
2. Depositor: Hyo Jeong, HONG (Inventor):
   Clover Apt. 117-2012, Dunsan-dong, Seo-Ku, Taeion 302-772, Republic of Korea.
3. The date of Deposit: Mar. 13, 2002 (both microorganisms).
4. Accession numbers: KCTC 10198BP, KCTXC 10199BP.
5. The date of viability test: Jan. 17,2005 (KCTC 10198BP0 Jan. 21, 2005 (KCTS 10199BP).

The genes of humanized antibody heavy chain and light chain thus prepared may be inserted to pdCMV-dhfrC-HAV6 vector (KCTC 10028BP) to obtain an expression vector pdCMV-dhfrC-HuKR127 which can express both humanized antibody heavy chain HuKR127HC and light chain HZKR127I. The expression vector of the present invention may be introduced into microorganism, e.g., *E. coli* DH5α according to a conventional transformation method to obtain transformants *E. coli* DH5α/pdCMV-dhfrC-HuKR127. The transformants *E. coli* DH5α/pdCMV-dhfrC-HuKR127 was deposited on Mar. 13, 2002 with the Korean Collection for Type Cultures(KCTC)(Address: Korea Research Institute of Bioscience and Biotechnology(KRIBB), #52, Oun-dong, Yusong-ku, Taejon, 305-333, Republic of Korea) under the accession number, KCTC 10198BP, in accordance with the terms of Budapest Treaty on the International Recognition of the Deposit of Microorganism for the Purpose of Patent Procedure.

Meanwhile, CHO/HuKR127, CHO (Chinese hamster ovary) cell line transfected with vector pdCMV-dhfrC-HuKR127, was deposited on Mar. 13, 2002 with the Korean Collection for Type Cultures(KCTC) under the accession number, KCTC 10199BP, in accordance with the terms of Budapest Treaty on the International Recognition of the Deposit of Microorganism for the Purpose of Patent Procedure.

The humanized antibody HuKR127 of the present invention produced by culturing the CHO/HuKR127 cell line has a higher affinity to antigen and is expected to reduce HAMA (human anti-mouse antibody) response to a greater extent than the conventional antibody prepared according to the CDR-grafting method.

Accordingly, the humanized antibody of the present invention can be used in preventing hepatitis B virus infection and treating chronic Hepatitis B.

Thus, for preventing hepatitis B virus infection and treating chronic Hepatitis B, a pharmaceutical formulation of the inventive humanized antibody may be prepared in accordance with any of the conventional procedures.

The pharmaceutical composition of the present invention can be administered via various routes including intravenous and intramuscular introduction. It should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

The following Examples are intended to further illustrate the present invention without limiting its scope.

EXAMPLE 1

Preparation of Mouse/Human Chimeric Heavy Chain Gene

The gene encoding leader sequence and the γ1 constant region of the human antibody heavy chain were separately prepared by carrying out PCR using pCMV-HKR127HC ((Korean Patent No. 246128, KCTC 0531BP) as a template and a primer set of Ryu94 (SEQ ID NO: 5) and HUR43-1 (SEQ ID NO: 6) or HUR46-1 (SEQ ID NO: 9) and HUR31 (SEQ ID NO: 10).

The gene encoding heavy chain variable region of the murine monoclonal antibody KR127 was prepared by carrying out PCR using pKR127H(Korean Patent No. 250832, KCTC 0333BP) as a template and primers HUR44-1(SEQ ID NO: 7) and HUR45-1(SEQ ID NO: 8).

```
Ryu94:
5'-GAG AAT TCA CAT TCA CGA TGT ACT TG-3'

HUR43-1:
5'-CTG CTG CAG CTG GAC CTG ACT CTG GAC ACC ATT-3'

HUR44-1:
5'-CAG GTC CAG CTG CAG CAG TCT GGA CCT GAA CTG-3'

HUR45-1:
5'-TGG GCC CTT GGT GGA GGC TGC AGA GAC AGTGAC-3'

HUR46-1:
5'-GCC TCC ACC AAG GGC CCA TCG GTC TTC CCC CTG-3'

HUR31:
5'-CAG CGG CCG CTC ATT TAC CCG GGG ACA G-3'
```

Each PCR reaction was carried out using 10 ng of template, 1 μl of each primer (50 ppm), 0.5 μl of Pfu DNA polymerase (Promega), 4 μl of 2.5 mM dNTPmix and 5 μl of 10× Pfu reaction buffer solution. After pre-denaturation at 95° C. for 5 minutes, a PCR cycle was repeated 25 times, the cycle being composed of: 95° C. for 30 sec., 50° C. for 30 sec. and 72° C. for 45 sec. After annealing the DNA fragment obtained by using primers Ryu94 and HUR43-1, the DNA fragment obtained by using primers HUR44-1 and HUR45-1, and the DNA fragment obtained by using primers HUR46-1 and HUR31 were recombined by conducting recombinant PCR using primers Ryu94 and HUR31. The recombinant PCR reaction was carried out using the same reaction buffer solution as used above. After pre-denaturation at 95° C. for 5 minutes, a PCR cycle was repeated 30 times, the cycle being composed of: 95° C. for 30 sec., 50° C. for 30 sec. and 72° C. for 60 sec., and finally, the extension reaction was carried out at 72° C. for 5 min.

The chimeric heavy chain gene thus prepared was cleaved with EcoRI(GAATTC) and NdeI (GCGGCCGC) and inserted at the EcoRI/NdeI section of vector pcDdA (plasmid which is removed ApaI site in the multiple cloning site of pcDNA received from Invitrogen), to obtain vector pcDdAchKR127HC (FIG. 1). The base sequence of the chimeric heavy chain variable region gene (KR127VH) was confirmed by DNA sequence analysis (FIG. 2).

EXAMPLE 2

Preparation of Mouse/Human Chimeric Light Chain Gene

The gene encoding reader sequence and the constant region of the human antibody light chain were each prepared by carrying out PCR using pKC-dhfr-HKR127 (Korean Patent No. 2000-33008, KCTC 0529BP) as a template and a primer set of Ryu86 (SEQ ID NO: 11) and HUR48 (SEQ ID NO: 12) or HUR51 (SEQ ID NO: 15) and CK1D (SEQ ID NO: 16).

The gene encoding light chain variable region of the murine monoclonal antibody KR127 was prepared by carrying out PCR using pKR127K (Korean Patent No. 250832, KCTC 0334BP) as a template and primers HUR49 (SEQ ID NO: 13) and HUR50 (SEQ ID NO: 14).

```
Ryu86:
5'-CAA AGC TTG GAA GCA AGA TGG ATT CA-3'

HUR48:
5'-CAA GAT ATC CCC ACA GGT ACC AGA TAC-3'
```

```
HUR49:
5'-TGT GGG GAT ATC TTG ATG ACC CAA ACT-3'

HUR50:
5'-CAC AGA TCT TTT GAT TTC CAG CTT GGT-3'

HUR51:
5'-ATC AAA AGA TCT GTG GCT GCA CCA TCT-3'

CK1D:
5'-GCG CCG TCT AGA ATT AAC ACT CTC CCC TGT TGA AGC
TCT TTG TGA CGG GCG AACTCAG-3'
```

Each PCR reaction was carried out according to the method described in Example 1 except that primers Ryu86 and CK1D were used to ligate the annealed DNA fragments obtained by PCR reactions.

The chimeric light chain gene thus prepared was cleaved with HindIII (AAGCTT) and XbaI (TCTAGA) and inserted at the HindIII/XbaI section of vector pBluescript KS, to obtain a recombinant plasmid. Subsequently, the recombinant plasmid was cleaved with HindIII and ApaI and inserted at the HindIII/ApaI section of vector pCMV-dhfr (KCTC 8671P), to obtain plasmid pKC-dhfr-chKR127(FIG. 3). The base sequence of the chimeric light chain varible region gene (KR127VK) was confirmed by DNA sequence analysis (FIG. 4).

EXAMPLE 3

Mutation of CDR of Chimeric KR127 Antibody Heavy Chain by Alanine Injection

To examine whether each amino acid residue of KR127 heavy chain HCDR1 (aa 31-35), HCDR2(aa 50-65) and HCDR3 (aa 95-102) binds to antigen, PCR reaction was carried out using vector pcDdA-chKR127HC as a template to prepare a modified gene, wherein an amino acid residue of CDR was replaced with alanine (the replaced amino acid residue No. was indicated as Kabat number) (see FIG. 2).

A forward primer YM001N of SEQ ID NO: 17 was designed to provide the sequence corresponding to the reader sequence at the 5'-end of the chimeric heavy chain gene and EcoRI restriction site, and a reverse primer YM003 of SEQ ID NO: 18 was designed to have the sequence corresponding to the N-terminal downstream of CH1 domain of human heavy chain gene and ApaI restriction site.

```
YM001N:
5'-CCG GAA TTC ACA TTC ACG ATG TAC TTG-3'

YM003:
5'-TGC CCC CAG AGG TGC T-3'
```

The 5'-end primer ym257 of SEQ ID NO: 19 (corresponding to nucleotide Nos. 80 to 112 of SEQ ID NO: 1) was designed to replace Ser31 of HCDR1 with alanine (S31A) and the 3'-end primer YM258 of SEQ ID NO: 20 (corresponding to nucleotide Nos. 101 to 71 of SEQ ID NO: 1), to replace AGT (coding for Ser) of nucleotide Nos. 91 to 93 of HCDRI gene with GCT (coding for alanine).

Each PCR reaction was carried out according to the method described in Example 1 except that primer sets, YM001N and Y4258; and ym258 and YM003, were used and also that primers YM001N and YM003 were used to recombine the annealed DNA fragments obtained by PCR.

The chimeric light chain gene thus prepared was cleaved with EcoRI and ApaI and inserted at the EcoRI/ApaI section of vector pcDdA-chKR127HC prepared in Example 1, to obtain pcDdA-chKR127HC-S31A. The base sequence of the humanized antibody heavy chain variable region gene was confirmed by DNA sequence analysis. Vectors containing mutants thus prepared are shown in Table 1.

In Table 1, primer and mutation positions are numbered based on the base sequence of SEQ ID NO: 1.

TABLE 1

| CDR | | primer | primer position | mutation position | mutant | vector |
|---|---|---|---|---|---|---|
| HCDR1 | F | ym257 | 80-112 | 91-93 | Ser(AGT)→ | pcDdA-chKR127HC-S31A |
|  | R | YM258 | 101-71 |  | Ala(GCT) |  |
|  | F | ym259 | 83-112 | 94-96 | Ser(TCT)→ | pcDdA-chKR127HC-S32A |
|  | R | YM260 | 106-73 |  | Ala(GCT) |  |
|  | F | ym261 | 86-117 | 97-99 | Trp(TGG)→ | pcDdA-chKR127HC-W33A |
|  | R | YM262 | 108-76 |  | Ala(GCG) |  |
|  | F | ym263 | 90-118 | 100-102 | Met(ATG)→ | pcDdA-chKR127HC-M33A |
|  | R | YM264 | 111-79 |  | Ala(GCG) |  |
|  | F | ym265 | 94-120 | 103-105 | Asn(AAC)→ | pcDdA-chKR127HC-N35A |
|  | R | ym266 | 112-81 |  | Ala(GCC) |  |
| HCDR2 | F | YM221 | 139-174 | 148-150 | Arg(CGG)→ | pcDdA-chKR127HC-R50A |
|  | R | YM222 | 158-128 |  | Ala(GCC) |  |
|  | F | YM225 | 143-178 | 151-153 | Ile(ATT)→ | pcDdA-chKR127HC-I51A |
|  | R | YM226 | 162-131 |  | Ala(GCT) |  |
|  | F | YM227 | 145-180 | 154-156 | Tyr(TAT)→ | pcDdA-chKR127HC-Y52A |
|  | R | YM228 | 165-135 |  | Ala(GCT) |  |
|  | F | ym229 | 148-181 | 157-159 | Pro(CCT)→ | pcDdA-chKR127HC-P52aA |
|  | R | YM230 | 167-136 |  | Ala(GCT) |  |
|  | F | ym231 | 150-186 | 160-162 | Gly(GGA)→ | pcDdA-chKR127HC-G53A |
|  | R | YM232 | 173-145 |  | Ala(GCA) |  |
|  | F | ym233 | 152-188 | 163-165 | Asp(GAT)→ | pcDdA-chKR127HC-D54A |
|  | R | YM234 | 176-144 |  | Ala(GCT) |  |
|  | F | ym235 | 155-193 | 166-168 | Gly(GGA)→ | pcDdA-chKR127HC-G55A |
|  | R | YM236 | 178-146 |  | Ala(GCA) |  |
|  | F | ym237 | 158-194 | 169-171 | Asp(GAT)→ | pcDdA-chKR127HC-D56A |
|  | R | ym238 | 184-149 |  | Ala(GCT) |  |
|  | F | ym239 | 160-195 | 172-174 | Thr(ACT)→ | pcDdA-chKR127HC-T57A |
|  | R | ym240 | 185-150 |  | Ala(GCT) |  |
|  | F | ym241 | 164-196 | 175-177 | Asn(AAC)→ | pcDdA-chKR127HC-N58A |
|  | R | ym242 | 187-150 |  | Ala(GCC) |  |

TABLE 1-continued

| CDR | primer | | primer position | mutation position | mutant | vector |
|---|---|---|---|---|---|---|
| HCDR3 | F | YM207 | 286-317 | 295-297 | Glu(GAG)→Ala(GCG) | pcDdA-chKR127HC-E95A |
| | R | YM208 | 305-274 | | | |
| | F | YM209 | 289-316 | 298-300 | Tyr(TAC)→Ala(GCC) | pcDdA-chKR127HC-Y96A |
| | R | YM210 | 307-276 | | | |
| | F | YM211 | 292-318 | 301-303 | Asp(GAC)→Ala(GCC) | pcDdA-chKR127HC-D97A |
| | R | YM212 | 313-279 | | | |
| | F | YM213 | 296-321 | 304-306 | Glu(GAG)→Ala(GCG) | pcDdA-chKR127HC-E98A |
| | R | YM214 | 315-285 | | | |
| | F | YM255 | 303-327 | 310-312 | Tyr(TAC)→Ala(GGC) | pcDdA-chKR127HC-Y102A |
| | R | YM256 | 319-289 | | | |

TEST EXAMPLE 1

Expression of Chimeric Antibody Having a Modified Heavy Chain and Its Affinity to Antigen (Step 1) Expression of Chimeric Antibody COS7 cells (ATCC CRL-165 1) were seeded to DMEM media (GIBCO) containing 10% bovine serum and subcultured in an incubator at 37° C. under an atmosphere of 5% $CO_2$. $1 \times 10^6$ cells thus obtained were seeded to the same media and incubated at 37° C. overnight. Thus, 5 µg of plasmid pKC-dhfr-chKR127 (expressing chimeric light chain) obtained in Example 2, 5 µg of plasmid obtained in Example 3 were diluted with OPTI-MEMI(GIBCO) to 800 µl. 50 µl of Lipofectamine (GIBCO) were diluted with the same solution to 800 µl. The resulting solutions were added to a 15 µl tube, mixed and then, kept at room temperature for more than 15 minutes. Meanwhile, COS7 cells incubated as above were washed three times with OPTI-MEM I. Then, 6.4 ml of OPTI-MEM I was added to the DNA-Lipofectamine mixture and the resulting solution was evenly distributed on the COS7 cells, which were cultured for 48 hours in a 5% $CO_2$ incubator to obtain a supernatant. The resulting solution was subjected to sandwich ELISA analysis using anti-human IgG (Sigma) as a capture antibody and anti-human antigen (Fc-specific)-horseradish peroxidase (PIERCE) as a secondary antibody to confirm the expression of the chimeric antibody.

(Step 2) Affinity to Antigen 150 ng of HBV recombinant antigen GST-pre-S1(1-56) (H. S. Kim and H. J. Hong, *Biotechnology Letters*, 17, 871-876(1995)) was coated to each well of a microplate and 5 ng of the supernatant obtained in Step 1 was added to each well. The resulting solution was subjected to indirect ELISA using the same secondary antibody as used in step 1, followed by measuring the absorbance at 450 nm. Further, the affinity to antigen ($K_D$) of each modified heavy chain was determined by competitive ELISA method (Ryu et al., *J. Med. Virol.*, 52, 226(1997)) and compared with that of pCK-dhfr-chKR127 containing wildtype chimeric heavy chain. The result is shown in Table 2.

TABLE 2

| CDR | Mutant | $K_D$ (nM) |
|---|---|---|
| | WT | 11.0 ± 1.664 |
| H1 | S31A | 14.67 ± 2.386 |
| | S32A | 8.455 ± 0.840 |
| | W33A | >10000 |
| | M34A | >10000 |
| | N35A | >10000 |

TABLE 2-continued

| CDR | Mutant | $K_D$ (nM) |
|---|---|---|
| H2 | R50A | >10000 |
| | I51A | 12.8 ± 1.05 |
| | Y52A | 276.8 ± 23.60 |
| | P52aA | 170.3 ± 5.318 |
| | G53A | 7.697 ± 0.980 |
| | D54A | 1.663 ± 0.477 |
| | G55A | 5.766 ± 0.211 |
| | D56A | 6.59 ± 1.09 |
| | T57A | 13.68 ± 4.016 |
| | N58A | 1.568 ± 0.085 |
| H3 | E95A | >10000 |
| | Y96A | >10000 |
| | D97A | 0.57 ± 0.03 |
| | E98A | 64.2 ± 7.78 |
| | Y102A | 3.581 ± 0.457 |

As shown in Table 2, the affinities to antigen of the mutants obtained by replacing Trp33, Met34, or Asn35 of HCDR1; Arg50, Tyr52, or Pro52a of HCDR2; Glu95, Tyr96, or Glu98 of HCDR3 with alanine were more than 3 times lower than that of wild type. However; a mutant having alanine substituting for Asp97 or Tyr102 residue of HCDR3 exhibited an enhanced affinity to antigen.

EXAMPLE 4

Preparation of HCDR3 Mutants and Their Affinities to Antigen (Step 1) D97R and E98V Mutants Each mutant was prepared by replacing Asp97 or Glu98 of HCDR3 with arginine as a positively charged amino acid (it is represented as "D97R") or valine as a neutral amino acid (it is represented as "E98V") according to the site-directed mutagenesis as used in Example 3. Vectors containing mutants prepared as above are shown in Table 3.

TABLE 3

| CDR | primer | | primer position | mutation position | mutant | vector |
|---|---|---|---|---|---|---|
| HCDR3 | R | P1 | 312-279 | 301-303 | Asp(GAC)→Arg(CGG) | pcDdA-chKR127HC-D97R |
| | F | P2 | 295-326 | | | |
| | R | P3 | 312-279 | 301-303 | Asp(GAC)→Val(GTT) | pcDdA-chKR127HC-D97V |
| | F | P4 | 295-326 | | | |
| | R | P5 | 312-279 | 304-306 | Glu(GAG)→Arg(CGG) | pcDdA-chKR127HC-E98R |
| | F | P6 | 295-326 | | | |
| | R | P7 | 312-279 | 304-306 | Glu(GAG)→Val(GTT) | pcDdA-chKR127HC-E98V |
| | F | P8 | 295-326 | | | |

Then, each mutant thus obtained was measured for its affinity to antigen in according to the method described in Test Example 1 and compared with that of the wild type.

Figure 5:
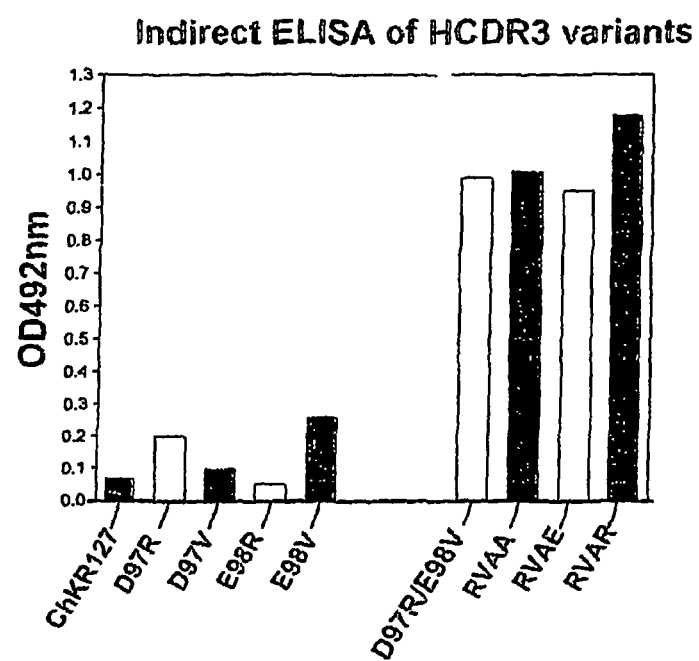
FIG. 5: the affinity to antigen of a humanized antibody having a heavy chain CDR mutant.

As shown in FIG. 5, the affinity to antigen of D97R was more than 3 times higher than that of the wild type, which the affinity to antigen of E98V, more than 4 times higher than that of the wild type. However, mutant E98R showed a low affinity to antigen.

(Step 2) D97R/E98V Mutant

To prepare D97R/E98V mutant containing both D97R and E98V, which were found to be mutants having high affinity to antigen, PCR reaction was carried out using pcDdA-chKR127HC-D97R which contains D97R gene as a template and primers P7 and P8.

Then, the D97R/E98V mutant thus obtained was measured for its affinity to antigen in according to the method described in Test Example 1.

As shown in FIG. 5, the affinity to antigen of D97R/E98V was more than 15 times higher than that of the wild type.

(Step 3) D97R/E98V/Y102A Mutant

To prepare D97R/E98V/Y102A mutant containing D97R, E98V and Y102A, PCR reaction was carried out using pcDdA-chKR127HC-RV containing D97R/E98V as a template and primers YM255 and YM256.

Then, the D97R/E98V/Y102A mutant (hereinafter "RVAA") thus obtained was measured for its affinity to antigen in according to the method described in Test Example 1.

As shown in FIG. 5, the affinity to antigen of D97R/E98V/Y102A was similar to that of D97R/E98V.

(Step 4) D97R/E98V/Y102E and D97R/E98V/Y102R Mutants

To prepare D97R/E98V/Y102E mutant and D97R/E98V/Y102R mutant, PCR reaction was carried out using pcDdA-chKR127HC-RV containing D97R/E98V as a template, and primer sets P17/P18 and P19/P20, respectively.

Vctor containing mutants prepared above are shown in Table 4.

TABLE 4

| | primer | primer position | mutation position | mutant | vector |
|---|---|---|---|---|---|
| HCDR3 | R P17 | 312-279 | 307-309 | Tyr(TAC)→ Glu(GAG) | pcDdA-chKR127HC-RVAE |
| | F P18 | 295-326 | | | |
| | R P19 | 312-279 | 307-309 | Tyr(TAC)→ Arg(CGT) | pcDdA-chKR127HC-RVAR |
| | F P20 | 295-326 | | | |

Then, D97R/E98V/Y102E mutant (hereinafter "RVAE") and D97R/E98V/Y102R mutant (hereinafter "RVAR") thus obtained were measured for respective affinities to antigen in according to the method described in Test Example 1.

As shown in FIG. 5, the affinity to antigen of RVAE was similar to that of RVAA, while the affinity to antigen of RVAR was higher than that of RVAA.

TEST EXAMPLE 2

Measurement of Affinity to Antigen of RVAR

The RVAR mutant prepared in step 4 of Example 4 was subjected to competitive ELISA to measure its affinity to antigen as follows:

COS7 cells were transfected with the plasmid prepared in step 4 of Example 4 and the plasmid expressing chimeric light chain(pKC-dhfr-chKR127) prepared in Example 2 to produce an antibody. 5 ng of the antibody thus obtained was reacted with pre-S1 antigen ($1 \times 10^{-7}$ to $1 \times 10^{-12}$ M) at 37° C. for 2 hours. The resulting solution was added to each well of a 96-well microplate coated with pre-S1 antigen and reacted at 37° C. for 30 minutes, and then the resulting solution was subjected to ELISA analysis according to the method described in Example 4. Used as a control is chimeric antibody (chKR127) obtained from COS7 cells transfected with pcDdA-chKR127HC and pKC-dhfr-chKR127.

The affinity to antigen of RVAR was about $1.8 \times 10^{-0}$ M, which is 45 times higher than that of chKR127, about $8.2 \times 10^{-9}$ M

EXAMPLE 5

Mutation of CDR of Chimeric KR127 Antibody Light Chain by Alanine Injection

To examine the affinity of each amino acid residue of KR127 light chain LCDR1 (aa 24-34), LCDR2(aa 50-60) and LCDR3 (aa 89-97) to antigen, PCR reaction was carried out using vector pKC-dhfr-chKR127 as a template to prepare a modified gene having each amino acid residue of CDR replaced with alanine (the replaced amino acid residue Number was indicated as Kabat number)(see FIG. 2).

Forward primer YM004 of SEQ ID NO: 21 was designed to provide the sequence corresponding to the reader sequence at the 5'-end of the chimeric light chain gene and the HindIII restrition site, and a reverse primer YM009 of SEQ ID NO: 22 was designed to have the sequence corresponding to the N-terminal region of human light chain gene and the BsiWI (CGTACG) restriction site. These primers were used in preparation of mutants of light chain CDR residue.

YM004:

5'-CCA AAG CTT GGA AAG ATG GAT TCA CAG-3'

YM009:

5'-GCA GCC ACC GTA CGT TTG ATT TCC ACC TTG GT-3'

Forward primer YM135 was designed to replace Ser26 of LCDR1 with alanine (S26A) and a reverse primer YM136, to replace AGT coding for Ser at the nucleotide Nos. 76 to 78 of LCDRI gene with GCT coding for alanine.

PCR reactions were carried out according to the method described in Example 1 except that primer sets, YM004/YM135, and YM136/YM009, were used and that primers YM004 and YM009 were used to recombine the annealed DNA fragments obtained by PCR.

The variable region gene of the mutant thus prepared was cleaved with HindIII and BsiWI and inserted at the HindIII/BsiWI section of vector pKC-dhfr-chKR127, to obtain pKC-dhfr-chKR127BS-S26A. The base sequence of the modified chimeric light chain variable region gene was confirmed by DNA sequence analysis. The vectors containing mutants prepared above are shown in Table 5.

In Table 5, the primer and mutation positions are numbered based on the base sequence of SEQ ID NO: 3.

TABLE 5

| | | primer | primer position | mutation position | mutant | vector |
|---|---|---|---|---|---|---|
| LCDR1 | F | YM135 | 67-102 | 76-78 | Ser(AGT)-Ala(GCT) | pKC-dhfr-chKR127BS-S26A |
| | R | YM136 | 86-54 | | | |
| | F | YM137 | 69-107 | 79-81 | Gln(CAG)-Ala(GCG) | pKC-dhfr-chKR127BS-Q27A |
| | R | YM138 | 91-56 | | | |
| | F | YM139 | 70-111 | 82-84 | Ser(AGC)-Ala(GCC) | pKC-dhfr-chKR127BS-S27aA |
| | R | YM140 | 94-58 | | | |
| | F | YM141 | 73-114 | 85-87 | Leu(CTC)-Ala(GCC) | pKC-dhfr-chKR127BS-L27bA |
| | R | YM142 | 98-64 | | | |
| | F | YM143 | 73-116 | 88-91 | Leu(TTA)-Ala(GCA) | pKC-dhfr-chKR127BS-L27cA |
| | R | YM144 | 102-68 | | | |
| | F | YM145 | 79-118 | 91-93 | Tyr(TAT)-Ala(GCT) | pKC-dhfr-chKR127BS-Y27dA |
| | R | YM146 | 103-69 | | | |
| | F | YM147 | 83-119 | 94-96 | Ser(AGT)-Ala(GCT) | pKC-dhfr-chKR127BS-S27eA |
| | R | YM148 | 107-69 | | | |
| | F | YM149 | 84-120 | 97-99 | Asn(AAT)-Ala(GCT) | pKC-dhfr-chKR127BS-N28A |
| | R | YM150 | 110-70 | | | |
| | F | YM151 | 88-127 | 100-102 | Gly(GGA)-Ala(GCA) | pKC-dhfr-chKR127BS-G29A |
| | R | YM152 | 114-74 | | | |
| | F | YM153 | 91-130 | 103-105 | Lys(AAA)-Ala(GCA) | pKC-dhfr-chKR127BS-K30A |
| | R | YM154 | 116-77 | | | |
| | F | YM155 | 93-132 | 106-108 | Thr(ACC)-Ala(GCC) | pKC-dhfr-chKR127BS-T31A |
| | R | YM156 | 118-80 | | | |
| | F | YM103 | 99-133 | 109-111 | Tyr(TAT)-Ala(GCT) | pKC-dhfr-chKR127BS-Y32A |
| | R | YM104 | 120-83 | | | |
| | F | N34A-F | 106-132 | 115-118 | Asn(AAT)-Ala(GCT) | pKC-dhfr-chKR127BS-Y34A |
| | R | N34A-R | 126-100 | | | |
| LCDR2 | F | YM129 | 151-188 | 163-165 | Leu(CTG)-Ala(GCG) | pKC-dhfr-chKR127BS-L50A |
| | R | YM130 | 175-140 | | | |
| | F | YM131 | 153-191 | 166-168 | Val(GTG)-Ala(GCG) | pKC-dhfr-chKR127BS-V51A |
| | R | YM132 | 179-145 | | | |
| | F | YM133 | 157-192 | 169-171 | Ser(TCT)-Ala(GCT) | pKC-dhfr-chKR127BS-S52A |
| | R | YM134 | 181-147 | | | |
| | F | K53A-F | 163-187 | 172-174 | Lys(AAA)-Ala(GCA) | pKC-dhfr-chKR127BS-K53A |
| | R | K53A-R | 178-154 | | | |
| | F | L54A-F | 163-189 | 175-177 | Leu(CTG)-Ala(GCG) | pKC-dhfr-chKR127BS-L54A |
| | R | L54A-R | 180-159 | | | |
| | F | D55A-F | 170-195 | 178-180 | Asp(GAC)-Ala(GCC) | pKC-dhfr-chKR127BS-D55A |
| | R | D55A-R | 184-163 | | | |
| | F | K56A-F | 175-198 | 181-183 | Ser(TCT)-Ala(GCT) | pKC-dhfr-chKR127BS-S56A |
| | R | K56A-R | 190-168 | | | |
| LCDR3 | F | YM113 | 270-304 | 280-282 | Val(GTG)-Ala(GCG) | pKC-dhfr-chKR127BS-V89A |
| | R | YM114 | 292-258 | | | |
| | F | YM115 | 274-307 | 283-285 | Gln(CAA)-Ala(GCA) | pKC-dhfr-chKR127BS-Q90A |
| | R | YM116 | 294-259 | | | |
| | F | YM117 | 277-310 | 286-288 | Gly(GGT)-Ala(GCT) | pKC-dhfr-chKR127BS-G91A |
| | R | YM118 | 296-265 | | | |
| | F | YM119 | 281-310 | 289-291 | Thr(ACA)-Ala(GCA) | pKC-dhfr-chKR127BS-T92A |
| | R | YM120 | 302-266 | | | |
| | F | YM121 | 282-313 | 292-294 | His(CAT)-Ala(GCT) | pKC-dhfr-chKR127BS-H93A |
| | R | YM122 | 304-271 | | | |
| | F | YM111 | 286-314 | 295-297 | Phe(TTT)-Ala(GCT) | pKC-dhfr-chKR127BS-F94A |
| | R | YM112 | 307-274 | | | |
| | F | YM123 | 286-317 | 298-300 | Pro(CCT)-Ala(GCT) | pKC-dhfr-chKR127BS-P95A |
| | R | YM124 | 308-278 | | | |
| | F | YM125 | 292-319 | 301-303 | Gln(CAG)-Ala(GCG) | pKC-dhfr-chKR127BS-Q96A |
| | R | YM126 | 311-279 | | | |
| | F | YM127 | 294-320 | 304-306 | Thr(ACG)-Ala(GCG) | pKC-dhfr-chKR127BS-T97A |
| | R | YM128 | 313-282 | | | |

TEST EXAMPLE 3

Measurement of Affinity to Antigen of Light Chain Mutant

COS7 cell was transfected with each of the light chain mutants prepared in Example 5 and the plasmid expressing chimeric heavy chain(pcDdA-chKR127HC) to produce an antibody. The antibody obtained was measured for its affinity to antigen in accordance with the method described in Test Example 1.

Table 6 shows the results obtained for the mutants and pdDA-chKR127HC containing wildtype chimeric KR127 heavy chain.

TABLE 6

| CDR | mutant | $K_D$ (nM) |
|---|---|---|
| L1 | S26A | 6.49 ± 0.244 |
| | Q27A | 14.2 ± 2.29 |
| | S27aA | 37.9 ± 6.66 |
| | L27bA | >10000 |
| | L27cA | 36.8 ± 11.01 |
| | Y27dA | 1032.7 ± 56.1 |
| | S27eA | >10000 |
| | N28A | >10000 |
| | G29A | 23.94 ± 2.62 |
| | K30A | >10000 |

TABLE 6-continued

| CDR | mutant | $K_D$ (nM) |
|---|---|---|
|  | T31A | 13.19 ± 1.98 |
|  | Y32A | >10000 |
|  | N34A | >10000 |
| L2 | L50A | 159.4 ± 21.37 |
|  | V51A | 37.00 ± 10.33 |
|  | S52A | 14.08 ± 0.509 |
|  | K53A | 7.928 ± 0.976 |
|  | L54A | 12.57 ± 2.453 |
|  | D55A | 225.2 ± 2.970 |
|  | S56A | 12.95 ± 0.367 |
| L3 | V89A | 121.2 ± 4.62 |
|  | Q90A | >10000 |
|  | G91A | >10000 |
|  | T92A | 74.2 ± 2.90 |
|  | H93A | 54.5 ± 4.48 |
|  | F94A | >10000 |
|  | P95A | >10000 |
|  | Q96A | 293.6 ± 7.13 |
|  | T97A | 17.3 ± 2.56 |

As shown in Table 6, the affinities to antigen of the mutants obtained by replacing the Leu27b, Tyr27d, Ser27e, Asn28, Lys30, Tyr32, and Asn34 of LCDR1; Leu50 and Asp55 of LCDR2; and Val89, Gln90, Gly91, Thr92, His93, Phe94, Pro95, and Gln96 of LCDR3 with alanine, respectively, were more than 3 times lower than that of the wild type. Therefore, these residues was determined as SDR.

EXAMPLE 6

Preparation of Humanized Heavy Chain by SDR-Grafting Method

A humanized heavy chain was prepared using DP7-JH4, a human heavy chain constructed by combining human immunoglobulin germline VH gene segment DP7 (Tomlinson et al., *J. Mol. Biol.*, 227, 776-798, 1992) having an amino acid sequence similar to KR127 heavy chain variable regions and human immunoglobulin germline JH4 segment (Ravetch et al., *Cell*, 27, 583-591 (1981)).

The Trp33 and Asn35 in HCDR1 of the KR127 were grafted into the DP7-JH4. The Met34 in HCDR1 of the KR127 is identical to that of DP7-JH4. Further, to inhibit lowering the affinity to antigen, Tyr32 in HCDR1 of the KR127 was replaced with alanine of HCDR1 of a human antibody (Gen Bank data base 75023 (SAWMN)).

The Arg50 and Tyr52 in HCDR2 of the KR127 were grafted onto the DP7-JH4. The Pro52a in HCDR2 of the KR127 is identical to that of DP7-JH4.

The Asp95, Tyr96, Arg97, Val98, and Arg102 of HCDR3 were grafted into DP7-JH4.

Further, Ala71 and Lys73 of FR 3 (framwork region 3) in the heavy chain variable region of KR127 antibody which affects the conformation of CDR loops were grafted thereto.

Then, PCR reaction was carried out using primers Ryu166 of SEQ ID NO: 23 and Hur37 of SEQ ID NO: 24 according to the method described in Example 3 to obtain a humanized heavy chain variable region gene, HuKR127VH-VII.

```
Ryu 166:
5'-GGA TTT GTC TGC AGT CAT TGT GGC TCT GCC CTG GAA
CTT-3'

Hur 37:
5'-GAC AAA TCC ACG AGC ACA GTC TAC ATG-3'
```

The base sequence of the humanized heavy chain variable region gene was determined by DNA sequence analysis (FIG. 2). Then, the gene was cleaved with EcoRI and ApaI and inserted at the EcoRI/ApaI section of vector pdDdA-chKR127HC to obtain pHuKR127HC.

A humanzied antibody was prepared by combining humanized heavy chain thus obtained and the humanized antibody HZKR127I light chain described in Korean Patent No. 246128 and measured the affinity to antigen was numbered according to the method described in Test Example 2. Humanized antibody HZKR127I was used as a control.

The affinity to antigen of the humanized antibody of about $1.5 \times 10^{-10}$ M was about 50 times higher than that of HZKR127I, about $8.2 \times 10^{-9}$ M.

EXAMPLE 7

Preparation of Humanized Light Chain by SDR-Grafting Method

A humanized light chain was prepared using DP7-JH4, a human light chian constructed by combining human immunoglobulin germline VK gene segment DPK12 (Cox et al., *Eur. J immunol.*, 24, 827-836 (1994)) having an amino acid sequence similar to KR127 light chain variable regions and human immunoglobulin germline JK4 segment (Hieter et al., *J. Biol. Chem.*, 257, 1516-1522 (1982)).

The Tyr27d, Asn28 and Asn34 in LCDR1 of KR127 were grafted into the DPK12-JK4. The amino acid residues at position 27b, 27e, 30 and 32 of DP7 is identical to those of KR127 light chain.

The Leu50 and Asp55 in LCDR2 of KR127 were grafted into the DPK12-JK4 gene.

The Val89, Gly91, Thr92, His93, Phe94, and Gln96 in LCDR3 of KR127 were grafted into the DPK12-JK4. The residues at positions 90 and 95 of DP7 is identical to those of KR127.

Further, Leu36 and Arg46 of FR 2 in the light chain variable region of KR127 antibody (which acts on interaction with heavy chain or CDR) were grafted thereto.

Then, PCR reaction was carried out using primers Ryu118 of SEQ ID NO: 25 and Ryu119 of SEQ ID NO: 26 according to the method described in Example 3 to prepare a humanized light chain variable region gene, HuKR127VH-IV.

```
Ryu 118:
5'-CTG TGG AGG CTG GCC TGG CTT CTG TAA TAA CCA-3'

Ryu 119:
5'-GGC CAG CCT CCA CAG CTC CTA ATC TAT CTG-3'
```

The base sequence of the humanized light chain variable region gene was determined by DNA sequence analysis (see HZIV of FIG. 4). Then, the gene was cleaved with HindIII and BsiWI and inserted at the HindIII/BsiWI section of vector pKC-dhfr-chKR127BS to obtain pHuKR127KC.

A humanized antibody was prepared by combining humanized light chain thus obtained and the humanized antibody HZKR127I heavy chain described in Korean Patent No. 246128 and its affinity to antigen was measured according to the method described in Test Example 2. Humanized antibody HZKR127I was used as a control.

The affinities to antigen of the humanized antibody of about $8.4 \times 10^{-9}$ M was similar to that of HZKR127I, about $8.2 \times 10^{-9}$ M.

EXAMPLE 8

Figure 6:
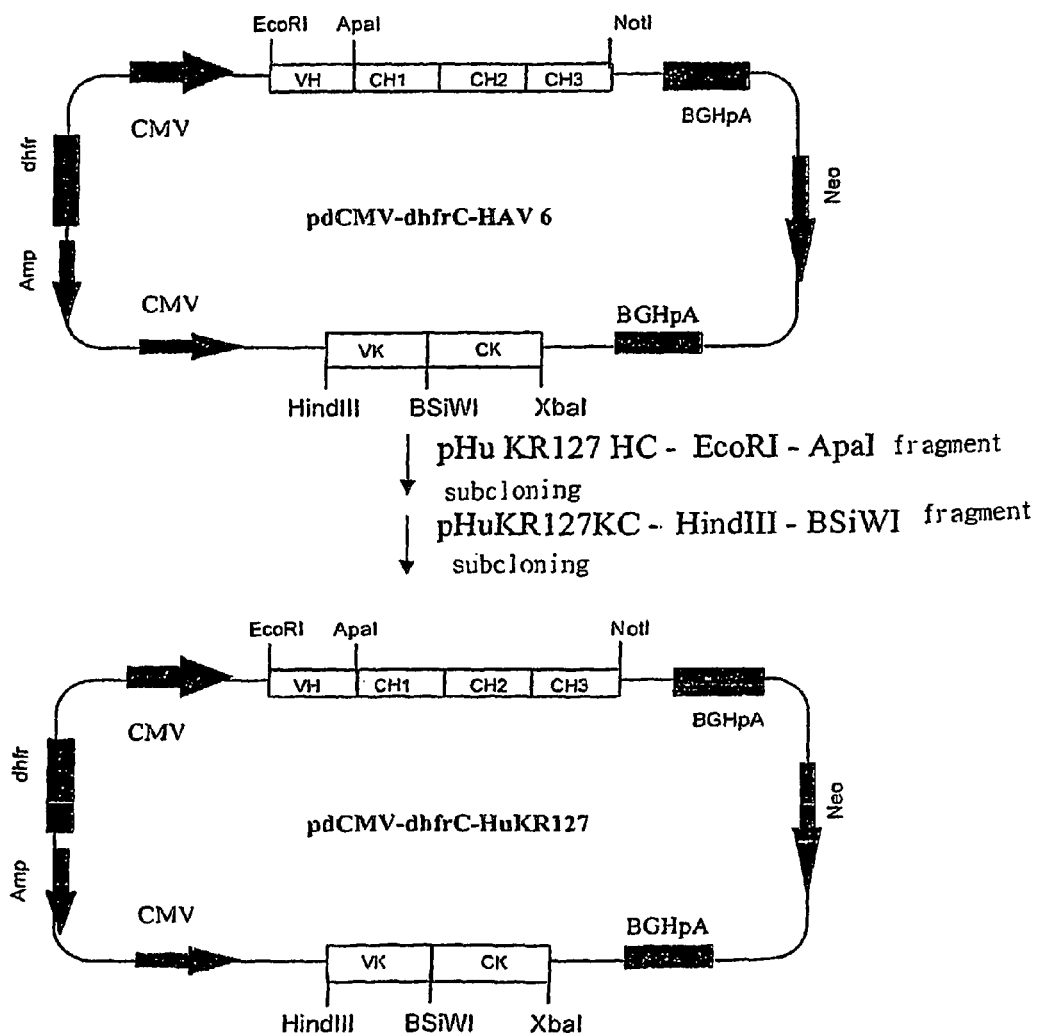
FIG. 6: the procedure for constructing an expression vector of the humanized antibody.

Preparation of Humanized Antibody and Measurement of the Affinity to Antigen To prepare a plasmid containing humanized heavy chain plasmid pHuKR127HC and humanized light chain plasmid pHuKR127KC, the EcoRI/ApaI fragment containing humanized heavy chain variable region gene of pHuKR127HC and the HindIII/BsiWI fragment containing humanized light chain variable region gene of pHuKR127KC were inserted at the EcoRI/ApaI and HindIII/BsiWI sections of vector pdCMV-dhfrC-HAV6 (KCTC 10028BP), respectively, to obtain plasmid pdCMV-dhfrC-HuKR127 (FIG. 6). *E. coli* DH5 α was transformed with the plasmid thus obtained and the transformed *E. coli* DH5α/pdCMC-dhfrC-HuKR127 was deposited on Mar. 13, 2002 with the Korean Collection for Type Cultures(KCTC)(Address: Korea Research Institute of Bioscience and Biotechnology(KRIBB), #52, Oun-dong, Yusong-ku, Taejon, 305-333, Republic of Korea) under the accession number, KCTC 10198BP, in accordance with the terms of Budapest Treaty on the International Recognition of the Deposit of Microorganism for the Purpose of Patent Procedure.

To prepare cell line expressing the humanized antibody, dhfr-defected CHO (chinese hamster ovary) cells were transformed with plasmid pdCMV-dhfrC-HuKR127 as follows:

CHO cells (ATCC CRL 9096) were seeded to DMEM/F12 media (GIBCO) containing 10% fetal bovine serum and sub-cultured in an incubator at 37° C. under an atmosphere of 5% $CO_2$. $5 \times 10^5$ cells thus obtained were seeded to the same media and incubated at 37° C. overnight, followed by washing 3 times with OPTI-MEMI solution (GIBCO).

Meanwhile, 5 μg of the plasmid pdCMV-dhfrC-HuKR127 was diluted in 500 μl of OPTI-MEMI solution. 25 μl of Lipofectamine was diluted in 500 μl of the same solution. The resulting solutions were added to a 15 ml tube, mixed, and then, kept at room temperature for more than 15 minutes. Then, 2 ml of OPTI-MEM I was added to by DNA-Lipofectamine mixture and the resulting solution was distributed evenly on the COS7 cells to be kept in a 5% $CO_2$ incubator at 37° C. for 6 hours. Added thereto was 3 ml of DMEM/F12 containing 20% fetal bovine serum and cultured for 48 hours.

Then, CHO cells were taken up with trypsin and cultured in a-MEM media(GIBCO) of 10% dialyzed fetal bovine serum containing G418 (GIBCO BRL, 550 mg/l) for 2 weeks. After confirming of antibody-producing ability of the transformed clone, the clone was cultured in a-MEM media of 10% dialyzed fetal bovine serum containing 20 nM MTX to induce amplification of gene.

Cell line CHO/HuKR127 having the highest antibody-productivity was selected from the clones and deposited on Mar. 13, 2002 with the Korean Collection for Type Cultures (KCTC) under the accession number, KCTC 10199BP, in accordance with the terms of Budapest Treaty on the International Recognition of the Deposit of Microorganism for the Purpose of Patent Procedure.

To measure the affinity to antigen of the humanized antibody HuKR127, CHO cell line thus obtained was mass cultured in a serum-absence media (CHO-SFMII, GIBCO) and subjected to protein G-shepharose 4B column (Pharmacia). Then, the antibody absorbed on the column was eluted with 0.1 M glycine solution (pH 2.7) and neutralized with 1.0 M tris solution (pH 9.0), followed by dialyzing in PBS buffer (pH 7.0). Further, the affinity to antigen of the purified antibody was determined by the competitive ELISA method described in Test Example 2 and compared with that of a control, humanized HuKR127I. The result was shown in FIG. 7.

Figure 7:
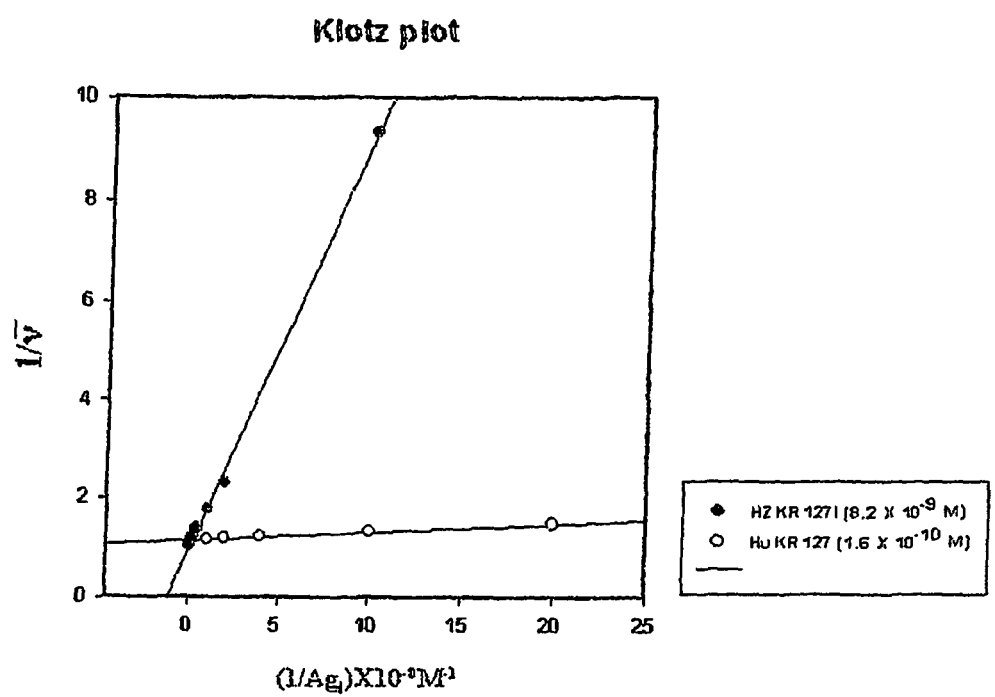
FIG. 7 shows the results of analysis for MHC class II-binding peptide sequences in heavy chain variable regions of HuKR127 and light chain variable regions of HuKR127, respectively, which are compared with HzKR127l, respectively.

As shown in FIG. 7, the affinity to antigen of the humanized antibody of the present invention of $1.6 \times 10^{-10}$ M was about 50 times higher than $8.2 \times 10^{-9}$ M3 of the control group.

EXAMPLE 9

Confirmation of Immune-Response Induction of Humanized Antibody

To confirm whether the humanized antibody of the present invention (HuKR127) prevents HAMA response, an analysis was conducted according to the TEPITOPE method (Sturniolo et al., *Nature Biotechnology*, 17, 555-561, 1999) to examine whether a peptide sequences which can bind to MHC (major histocompatibility complex) class II exists in the heavy and light chain variable regions of the humanized antibody.

Tables. 7 and 8 show the results of such analysis for MHC class II-binding peptide sequences in the heavy chain variable regions of HuKR127 and the light chain variable regions of HuKR127, respectively.

TABLE 7

| | HzKR127I | | HuKR127 | |
|---|---|---|---|---|
| antiboby | peptide | MHC class II | peptide | MHC class II |
| MHC class II-binding | LVQSGAEVV | DRB1_0306 | LVQSGAEVK | 0 |
| | | DRB1_0307 | | |
| | | DRB1_0308 | | |
| | | DRB1_0311 | | |
| | | DRB1_0421 | | |
| | | DRB1_0701 | | |
| | | DRB1_0703 | | |
| | VKPGASVKV | DRB1_0102 | KKPGASVKV | 0 |
| | FSSSWMNWV | DRB1_0703 | FTSAWMNWV | 0 |
| | WIGRIYPGD | DRB1_0801 | WMGRIYPSG | 0 |
| | | DRB1_0817 | | |
| | FQGKATLTA | DRB1_0401 | FQGRVTMTA | DRB1_0305 |
| | | DRB1_0402 | | DRB1_0401 |
| | | DRB1_0405 | | DRB1_0402 |
| | | DRB1_0408 | | DRB1_0408 |
| | | DRB1_0421 | | DRB1_0426 |
| | | DRB1_0426 | | DRB1_0801 |
| | | DRB1_0801 | | DRB1_0802 |
| | | DRB1_0802 | | DRB1_0804 |
| | | DRB1_0804 | | DRB1_0806 |
| | | DRB1_0806 | | DRB1_0813 |
| | | DRB1_0813 | | DRB1_0817 |
| | | DRB1_0817 | | DRB1_1101 |
| | | DRB1_1101 | | DRB1_1114 |
| | | DRB1_1102 | | DRB1_1120 |
| | | DRB1_1104 | | DRB1_1128 |
| | | DRB1_1106 | | DRB1_1302 |
| | | DRB1_1114 | | DRB1_1305 |
| | | DRB1_1120 | | DRB1_1307 |
| | | DRB1_1121 | | DRB1_1321 |
| | | DRB1_1128 | | DRB1_1323 |
| | | DRB1_1302 | | DRB1_1502 |
| | | DRB1_1305 | | |
| | | DRB1_1307 | | |
| | | DRB1_1311 | | |
| | | DRB1_1321 | | |
| | | DRB1_1322 | | |
| | | DRB1_1323 | | |
| | YWGQGTLVT | DRB1_0401 | RWGQGTLVT | 0 |
| | | DRB1_0405 | | |
| | | DRB1_0421 | | |
| | | DRB1_0426 | | |

TABLE 7-continued

| antiboby | HzKR127I peptide | MHC class II | HuKR127 peptide | MHC class II |
|---|---|---|---|---|
| | IGRIYPGDG | DRB5_0101<br>DRB5_0105 | MGRIYPSGG | DRB1_0404<br>DRB1_0405<br>DRB1_0410<br>DRB1_0423 |
| | YAQKFQGKA | DRB1_0802 | YAQKFQGRV | 0 |
| | VYFCAREYD | DRB1_1304 | VYYCAREYR | DRB1_0301 |
| | YWGQGTLVT | DRB1_0401<br>DRB1_0405<br>DRB1_0421<br>DRB1_0426 | RWGQGTLVT | 0 |
| total | | 50 | | 26 |

TABLE 8

| antiboby | HzKR127I peptide | MHC class II | HuKR127 peptide | MHC class II |
|---|---|---|---|---|
| a | | | | |
| MHC class II-binding | ILMTQTPLS | DRB1_0301<br>DRB1_0305<br>DRB1_0306<br>DRB1_0307<br>DRB1_0308<br>DRB1_0309<br>DRB1_0311<br>DRB1_0401<br>DRB1_0402<br>DRB1_0404<br>DRB1_0405<br>DRB1_0408<br>DRB1_0410<br>DRB1_0421<br>DRB1_0423<br>DRB1_0426<br>DRB1_0804<br>DRB1_1101<br>DRB1_1102<br>DRB1_1104<br>DRB1_1106<br>DRB1_1107<br>DRB1_1114<br>DRB1_1121<br>DRB1_1128<br>DRB1_1301<br>DRB1_1304<br>DRB1_1305<br>DRB1_1307<br>DRB1_1311<br>DRB1_1321<br>DRB1_1322<br>DRB1_1323<br>DRB1_1327<br>DRB1_1328 | IVMTQTPLS | 0 |
| | LMTQTPLSL | DRB1_0101<br>DRB1_0102<br>DRB1_1304 | VMTQTPLSL | 0 |
| | WLLQKPGQS | DRB1_0101<br>DRB1_0305<br>DRB1_0309<br>DRB1_0401<br>DRB1_0408<br>DRB1_0421<br>DRB1_0426<br>DRB1_0802<br>DRB1_1101<br>DRB1_1107<br>DRB1_1114<br>DRB1_1120<br>DRB1_1128<br>DRB1_1302<br>DRB1_1305<br>DRB1_1307<br>DRB1_1321<br>DRB1_1323<br>DRB5_0101<br>DRB5_0105 | WLLQKPGQP | 0 |
| | YYCVQGTHF | DRB1_0101<br>DRB1_0701<br>DRB1_0703<br>DRB5_0101<br>DRB5_0105 | YYCVQGTHF | DRB1_0101<br>DRB1_0701<br>DRB1_0703<br>DRB5_0101<br>DRB5_0105 |
| | YCVQGTHFP | DRB1_0401<br>DRB1_0421<br>DRB1_0426 | YCVQGTHFP | DRB1_0401<br>DRB1_0421<br>DRB1_0426 |
| b | | | | |
| | VGVYYCVQG | DRB1_0806 | VGVYYCVQG | DRB1_0806 |
| | IYLVSKLDS | DRB1_0301<br>DRB1_0305<br>DRB1_0306<br>DRB1_0307<br>DRB1_0308<br>DRB1_0309<br>DRB1_0311<br>DRB1_0405<br>DRB1_0410<br>DRB1_0801<br>DRB1_0802<br>DRB1_0804<br>DRB1_0806<br>DRB1_0813<br>DRB1_0817<br>DRB1_1101<br>DRB1_1102<br>DRB1_1104<br>DRB1_1106<br>DRB1_1107<br>DRB1_1114<br>DRB1_1120<br>DRB1_1121<br>DRB1_1128<br>DRB1_1301<br>DRB1_1302<br>DRB1_1304<br>DRB1_1305<br>DRB1_1307<br>DRB1_1311<br>DRB1_1321<br>DRB1_1322<br>DRB1_1323<br>DRB1_1327<br>DRB1_1328<br>DRB1_1501<br>DRB1_1506 | IYLVSNRDS | DRB1_0402<br>DRB1_0404<br>DRB1_0405<br>DRB1_0408<br>DRB1_0410<br>DRB1_0423<br>DRB1_0804<br>DRB1_1102<br>DRB1_1104<br>DRB1_1106<br>DRB1_1114<br>DRB1_1121<br>DRB1_1301<br>DRB1_1307<br>DRB1_1311<br>DRB1_1322<br>DRB1_1323<br>DRB1_1327<br>DRB1_1328<br>DRB5_0101<br>DRB5_0105 |
| | LIYLVSKLD | DRB1_0806<br>DRB1_1304<br>DRB1_1321 | LIYLVSNRD | DRB1_0401<br>DRB1_0404<br>DRB1_0405<br>DRB1_0408<br>DRB1_0410<br>DRB1_0421<br>DRB1_0423<br>DRB1_0426<br>DRB1_1304 |
| | YLVSKLDSG | 0 | YLVSNRDSG | DRB1_0309 |
| total | | 106 | | 40 |

As can be seen from Tables 8a-8b, the number of the peptide sequence in the humanized antibody HuKR127 which binds to MHC class II was fewer than of that the HzKR127I. These results suggest that humanized antibody HuKR127 of the present invention is expected to reduce HAMA response to a greater extent than HzKR127I.

While the embodiments of the subject invention have been described and illustrated, it is obvious that various changes and modifications can be made therein without departing from the spirit of the present invention which should be limited only by the scope of the appended claims.

What is claimed is:

1. A process for preparing a humanized antibody consisting of the steps of:

(a) first performing alanine scanning mutagenesis for replacing each amino acid residue in the entire complementarity determining region (CDR) of a murine monoclonal antibody variable regions that bind hepatitis B virus pre-S1 antigen with alanine to produce a series of transformants, selecting a transformant that has an affinity to antigen which is more than 3 times lower than the original murine antibody when replaced with alanine, determining the replaced amino acid residue of said transformant as a specificity determining residue (SDR), and (b) subsequently grafting all of the said SDRs to the corresponding amino acid sequence in human antibody heavy chain and light chain, wherein the CDR is selected from the group consisting of HCDR1(aa 31-35), HCDR2(aa 50-65) and HCDR3(aa 95-102) of the heavy chain (SEQ ID NO: 2); and LCDR1(aa 24-34), LCDR2 (aa 50-56) and LCDR3(aa 89-97) of the light chain (SEQ ID NO: 4) of the murine monoclonal antibody variable regions, and wherein the SDR is the Trp33, Met34, and Asn35 of HCDR1; Arg50, Tyr52, and Pro52a of HCDR2; and Glu95, Tyr96, and Glu98 of HCDR3 of the murine monoclonal antibody KR127 heavy chain.

2. The process of claim 1, which is characterized in that at least one of the following grafting steps is carried out:

the amino acid residue at position 32 in HCDR1 of human antibody is replaced with alanine;

the amino acid residue at position 97 in HCDR3 of human antibody is replaced with arginine or alanine;

the amino acid residue at position 98 in HCDR3 of human antibody is replaced with valine; and the amino acid residue at position 102 in HCDR3 of human antibody with arginine or alanine.

3. The process of claim 2, which is characterized in that the Trp33 and Asn35 of HCDR1; Arg50 and Tyr52 of HCDR2; and Arg95 and Tyr96 of HCDR3 of the murine monoclonal antibody KR127 heavy chain, are grafted into the human antibody heavy chain DP7-JH4.

4. The process of claim 3, which is characterized in that the amino acid residues of the A1a71 and Lys73 in Framework region 3 of the murine monoclonal antibody KR127 heavy chain variable region, are further grafted into the human antibody heavy chain DP7-JH4.

5. The process of claim 1, which is characterized in that the Leu27b, Tyr27d, Ser27e, Asn28, Lys30, Tyr32 and Asn34 of LCDR1; Leu50 and Asp55 of LCDR2; and Va189, GIn90, G1y91, Thr92, His93, Phe94, Pro95, and G1n96 of LCDR3 of the murine monoclonal antibody KR127 light chain, are grafted into the human antibody light chain.

6. The process of claim 5, which is characterized in that the Tyr27d, Asn28, Asn34 of LCDR1; Leu50 and Asp55 of LCDR2; and Va189, Gly91, Thr92, His93, Phe94, Pro95, and GIn96 of LCDR3 of the murine monoclonal antibody KR127 light chain, are grafted into the human antibody light chain DPK12-JK4.

7. The process of claim 5, which is characterized in that the Leu36 and Arg46 in Framework region 2 of the murine monoclonal antibody KR127 light chain variable region, are further grafted into the human antibody light chain DPK12-JK4.

* * * * *

SEQUENCE LISTING

```
<160> NUMBER OF SEQ ID NOS: 38

<210> SEQ ID NO 1
<211> LENGTH: 345
<212> TYPE: DNA
<213> ORGANISM: Artificial Sequence
<220> FEATURE:
<223> OTHER INFORMATION: Variable region of humanized light chain HZVII

<400> SEQUENCE: 1
caggtccagc tggtgcagtc tggagctgaa gtgaagaagc ctggggcctc agtgaaggtt      60
tcctgcaaag cttctggcta caccttcacc agtgcttgga tgaactgggt gcgacaggcc     120
cctggacagg gtcttgagtg gatgggacgg atttatccta gtggtggaag cactagctac     180
gcacagaagt tccagggcag agtcacaatg actgcagaca aatccacgag cacagtctac     240
atggagctca gcagcctgag atctgaggac acggcggtgt attactgtgc aagagagtac     300
cgggttgccc gttggggcca aggaactctg gtcactgtct cttca                     345

<210> SEQ ID NO 2
<211> LENGTH: 115
<212> TYPE: PRT
<213> ORGANISM: Artificial Sequence
<220> FEATURE:
<223> OTHER INFORMATION: Variable region of humanized light chain HZVII

<400> SEQUENCE: 2

Gln Val Gln Leu Val Gln Ser Gly Ala Glu Val Lys Ala Pro Gly Ala
  1               5                  10                  15

Ser Val Lys Val Ser Cys Lys Ala Ser Gly Tyr Thr Phe Thr Ser Ala
             20                  25                  30

Trp Met Asn Trp Val Arg Gln Ala Pro Gly Gln Gly Leu Glu Trp Met
         35                  40                  45

Gly Arg Ile Tyr Pro Ser Gly Gly Ser Thr Ser Tyr Ala Gln Lys Phe
     50                  55                  60

Gln Gly Arg Val Thr Met Thr Ala Asp Lys Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Tyr Arg Val Ala Arg Trp Gly Gln Gly Thr Leu Val Thr
            100                 105                 110

Val Ser Ala
        115

<210> SEQ ID NO 3
<211> LENGTH: 336
<212> TYPE: DNA
<213> ORGANISM: Artificial Sequence
<220> FEATURE:
<223> OTHER INFORMATION: Variable region of humanized light chain HZIV

<400> SEQUENCE: 3
gatatcgtga tgacccaaac tccactttct ttgtcggtta cccctggaca accagcctct      60
```

-continued

```
atctcttgca agtcaagtca gagcctctta tatagtaatg gaaaaaccta tttgaattgg    120
ttattacaga agccaggcca gcctccacag cgcctaatct atctggtgtc taatcgggac    180
tctggagtcc ctgacaggtt cagtggcagt ggatcaggaa cagattttac actgaaaatc    240
agcagagtgg aggctgagga tgttggagtt tattactgcg tgcaaggtac acattttcct    300
cagacgttcg gtggaggcac caaggtggaa atcaaa                              336
```

<210> SEQ ID NO 4
<211> LENGTH: 112
<212> TYPE: PRT
<213> ORGANISM: Artificial Sequence
<220> FEATURE:
<223> OTHER INFORMATION: Variable region of humanized light chain HZIV

<400> SEQUENCE: 4

```
Asp Ile Val Met Thr Gln Thr Pro Leu Ser Leu Ser Val Thr Pro Gly
  1               5                  10                  15

Gln Pro Ala Ser Ile Ser Cys Lys Ser Ser Gln Ser Leu Leu Tyr Ser
             20                  25                  30

Asn Gly Lys Thr Tyr Leu Asn Trp Leu Leu Gln Lys Pro Gly Gln Pro
         35                  40                  45

Pro Gln Arg Leu Ile Tyr Leu Val Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Thr His Phe Pro Gln Thr Phe Gly Gly Gly Thr Lys Val Glu Ile Lys
            100                 105                 110
```

<210> SEQ ID NO 5
<211> LENGTH: 26
<212> TYPE: DNA
<213> ORGANISM: Artificial Sequence
<220> FEATURE:
<223> OTHER INFORMATION: oligomer Ryu94

<400> SEQUENCE: 5

```
gagaattcac attcacgatg tacttg                                          26
```

<210> SEQ ID NO 6
<211> LENGTH: 33
<212> TYPE: DNA
<213> ORGANISM: Artificial Sequence
<220> FEATURE:
<223> OTHER INFORMATION: oligomer HUR43-1

<400> SEQUENCE: 6

```
ctgctgcagc tggacctgac tctggacacc att                                  33
```

<210> SEQ ID NO 7
<211> LENGTH: 33
<212> TYPE: DNA
<213> ORGANISM: Artificial Sequence
<220> FEATURE:
<223> OTHER INFORMATION: oligomer HUR44-1

<400> SEQUENCE: 7

```
caggtccagc tgcagcagtc tggacctgaa ctg                                  33
```

<210> SEQ ID NO 8
<211> LENGTH: 33

```
<212> TYPE: DNA
<213> ORGANISM: Artificial Sequence
<220> FEATURE:
<223> OTHER INFORMATION: oligomer HUR45-1

<400> SEQUENCE: 8
tgggcccttg gtggaggctg cagagacagt gac                                33

<210> SEQ ID NO 9
<211> LENGTH: 33
<212> TYPE: DNA
<213> ORGANISM: Artificial Sequence
<220> FEATURE:
<223> OTHER INFORMATION: oligomer HUR46-1

<400> SEQUENCE: 9
gcctccacca agggcccatc ggtcttcccc ctg                                 33

<210> SEQ ID NO 10
<211> LENGTH: 28
<212> TYPE: DNA
<213> ORGANISM: Artificial Sequence
<220> FEATURE:
<223> OTHER INFORMATION: oligomer HUR31

<400> SEQUENCE: 10
cagcggccgc tcatttaccc ggggacag                                      28

<210> SEQ ID NO 11
<211> LENGTH: 26
<212> TYPE: DNA
<213> ORGANISM: Artificial Sequence
<220> FEATURE:
<223> OTHER INFORMATION: oligomer Ryu86

<400> SEQUENCE: 11
caaagcttgg aagcaagatg gattca                                        26

<210> SEQ ID NO 12
<211> LENGTH: 27
<212> TYPE: DNA
<213> ORGANISM: Artificial Sequence
<220> FEATURE:
<223> OTHER INFORMATION: oligomer HUR48

<400> SEQUENCE: 12
caagatatcc ccacaggtac cagatac                                       27

<210> SEQ ID NO 13
<211> LENGTH: 27
<212> TYPE: DNA
<213> ORGANISM: Artificial Sequence
<220> FEATURE:
<223> OTHER INFORMATION: oligomer HUR49

<400> SEQUENCE: 13
tgtggggata tcttgatgac ccaaact                                       27

<210> SEQ ID NO 14
<211> LENGTH: 27
<212> TYPE: DNA
<213> ORGANISM: Artificial Sequence
<220> FEATURE:
<223> OTHER INFORMATION: oligomer HUR50

<400> SEQUENCE: 14
cacagatctt ttgatttcca gcttggt                                       27
```

```
<210> SEQ ID NO 15
<211> LENGTH: 27
<212> TYPE: DNA
<213> ORGANISM: Artificial Sequence
<220> FEATURE:
<223> OTHER INFORMATION: oligomer HUR51

<400> SEQUENCE: 15
atcaaaagat ctgtggctgc accatct                                         27

<210> SEQ ID NO 16
<211> LENGTH: 58
<212> TYPE: DNA
<213> ORGANISM: Artificial Sequence
<220> FEATURE:
<223> OTHER INFORMATION: oligomer CK1D

<400> SEQUENCE: 16
gcgccgtcta gaattaacac tctccctgt tgaagctctt tgtgacgggc gaactcag      58

<210> SEQ ID NO 17
<211> LENGTH: 27
<212> TYPE: DNA
<213> ORGANISM: Artificial Sequence
<220> FEATURE:
<223> OTHER INFORMATION: oligomer YM001N

<400> SEQUENCE: 17
ccggaattca cattcacgat gtacttg                                         27

<210> SEQ ID NO 18
<211> LENGTH: 16
<212> TYPE: DNA
<213> ORGANISM: Artificial Sequence
<220> FEATURE:
<223> OTHER INFORMATION: oligomer YM003

<400> SEQUENCE: 18
tgcccccaga ggtgct                                                     16

<210> SEQ ID NO 19
<211> LENGTH: 33
<212> TYPE: DNA
<213> ORGANISM: Artificial Sequence
<220> FEATURE:
<223> OTHER INFORMATION: oligomer ym257

<400> SEQUENCE: 19
acgcattcag tgcttcttgg atgaactggg tga                                  33

<210> SEQ ID NO 20
<211> LENGTH: 31
<212> TYPE: DNA
<213> ORGANISM: Artificial Sequence
<220> FEATURE:
<223> OTHER INFORMATION: oligomer YM258

<400> SEQUENCE: 20
atccaagaag cactgaatgc gtagccagaa g                                    31

<210> SEQ ID NO 21
<211> LENGTH: 38
<212> TYPE: DNA
<213> ORGANISM: Artificial Sequence
<220> FEATURE:
<223> OTHER INFORMATION: oligomer YM004
```

```
<400> SEQUENCE: 21
ccaattcaaa gcggtttttc cattactata taagaggc                           38

<210> SEQ ID NO 22
<211> LENGTH: 32
<212> TYPE: DNA
<213> ORGANISM: Artificial Sequence
<220> FEATURE:
<223> OTHER INFORMATION: oligomer YM009

<400> SEQUENCE: 22
gcagccaccg tacgtttgat ttccaccttg gt                                 32

<210> SEQ ID NO 23
<211> LENGTH: 39
<212> TYPE: DNA
<213> ORGANISM: Artificial Sequence
<220> FEATURE:
<223> OTHER INFORMATION: oligomer Ryu 166

<400> SEQUENCE: 23
ggatttgtct gcagtcattg tggctctgcc ctggaactt                          39

<210> SEQ ID NO 24
<211> LENGTH: 27
<212> TYPE: DNA
<213> ORGANISM: Artificial Sequence
<220> FEATURE:
<223> OTHER INFORMATION: oligomer Hur 37

<400> SEQUENCE: 24
gacaaatcca cgagcacagt ctacatg                                       27

<210> SEQ ID NO 25
<211> LENGTH: 33
<212> TYPE: DNA
<213> ORGANISM: Artificial Sequence
<220> FEATURE:
<223> OTHER INFORMATION: oligomer Ryu 118

<400> SEQUENCE: 25
ctgtggaggc tggcctggct tctgtaataa cca                                33

<210> SEQ ID NO 26
<211> LENGTH: 30
<212> TYPE: DNA
<213> ORGANISM: Artificial Sequence
<220> FEATURE:
<223> OTHER INFORMATION: oligomer Ryu 119

<400> SEQUENCE: 26
ggccagcctc cacagctcct aatctatctg                                    30

<210> SEQ ID NO 27
<211> LENGTH: 345
<212> TYPE: DNA
<213> ORGANISM: Artificial Sequence
<220> FEATURE:
<223> OTHER INFORMATION: Variable region of humanized heavy chain
      KR127VH

<400> SEQUENCE: 27
caggtccagc tgcagcagtc tggacctgaa ctggtgaagc ctggggcctc agtgaagatt   60
tcctgcaaag cttctggcta cgcattcagt agttcttgga tgaactgggt gaagcagagg  120
```

```
cctggacagg gtcttgagtg gattggacgg atttatcctg gagatggaga tactaactac    180
aatgggaagt tcaagggcaa ggccacactg actgcagaca atcctccag cacagcctac     240 atgcagctca gcagcctgac ctctgtggac tctgcggtct atttctgtgc aagagagtac    300
gacgaggctt actggggcca agggactctg gtcactgtct ctgca                   345
```

```
<210> SEQ ID NO 28
<211> LENGTH: 115
<212> TYPE: PRT
<213> ORGANISM: Artificial Sequence
<220> FEATURE:
<223> OTHER INFORMATION: Variable region of humanized heavy chain
      KR127VH

<400> SEQUENCE: 28

Gln Val Gln Leu Gln Gln Ser Gly Pro Glu Leu Val Lys Pro Gly Ala
 1               5                  10                  15

Ser Val Lys Ile Ser Cys Lys Ala Ser Gly Tyr Ala Phe Ser Ser Ser
             20                  25                  30

Trp Met Asn Trp Val Lys Gln Arg Pro Gly Gln Gly Leu Glu Trp Ile
         35                  40                  45

Gly Arg Ile Tyr Pro Gly Asp Gly Asp Thr Asn Tyr Asn Gly Lys Phe
     50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Val Asp Ser Ala Val Tyr Phe Cys
                 85                  90                  95

Ala Arg Glu Tyr Asp Glu Ala Tyr Trp Gly Gln Gly Thr Leu Val Thr
            100                 105                 110

Val Ser Ala
        115
```

```
<210> SEQ ID NO 29
<211> LENGTH: 336
<212> TYPE: DNA
<213> ORGANISM: Artificial Sequence
<220> FEATURE:
<223> OTHER INFORMATION: Variable region of humanized light chain
      KR127VK

<400> SEQUENCE: 29
gatatcttga tgacccaaac tccacttatt ttgtcggtta ccattggaca accagcctct     60
atctcttgca gtcaagtca gagcctctta tatagtaatg gaaaaaccta tttgaattgg    120
ttattacaga ggccaggcca gtctccaaag cgcctaatct atctggtgtc taaactggac    180
tctggagtcc ctgacaggtt cactggcagt ggatcaggaa cagattttac actgaaaatc    240
atcagagtgg aggctgagga tttgggagtt tattactgcg tgcaaggtac acatttttcct   300 cagacgttcg gtggaggcac caagctggaa atcaaa                             336
```

```
<210> SEQ ID NO 30
<211> LENGTH: 112
<212> TYPE: PRT
<213> ORGANISM: Artificial Sequence
<220> FEATURE:
<223> OTHER INFORMATION: Variable region of humanized light chain
      KR127VK

<400> SEQUENCE: 30

Asp Ile Leu Met Thr Gln Thr Pro Leu Ile Leu Ser Val Thr Ile Gly
 1               5                  10                  15
```

```
Gln Pro Ala Ser Ile Ser Cys Lys Ser Ser Gln Ser Leu Leu Tyr Ser
                20                  25                  30

Asn Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ile Arg Val Glu Ala Glu Asp Leu Gly Val Tyr Tyr Cys Val Gln Gly
                85                  90                  95

Thr His Phe Pro Gln Thr Phe Gly Gly Gly Thr Lys Leu Glu Ile Lys
            100                 105                 110

<210> SEQ ID NO 31
<211> LENGTH: 294
<212> TYPE: DNA
<213> ORGANISM: Artificial Sequence
<220> FEATURE:
<223> OTHER INFORMATION: Variable region of humanized heavy chain DP7

<400> SEQUENCE: 31
caggtgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag ggcttgagtg gatgggaata atcaacccta gtggtggtag cacaagctac     180
gcacagaagt tccagggcag agtcaccatg accagggaca cgtccacgag cacagtctac     240
atggagctga gcagcctgag atctgaggac acggccgtgt attactgtgc gaga           294

<210> SEQ ID NO 32
<211> LENGTH: 98
<212> TYPE: PRT
<213> ORGANISM: Artificial Sequence
<220> FEATURE:
<223> OTHER INFORMATION: Variable region of humanized heavy chain DP7

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 33
<211> LENGTH: 302
<212> TYPE: DNA
<213> ORGANISM: Artificial Sequence
<220> FEATURE:
<223> OTHER INFORMATION: Variable region of humanized light chain DPK12

<400> SEQUENCE: 33
gatattgtga tgacccagac tccactctct ctgtccgtca cccctggaca gccggcctcc      60
```

```
atctcctgca agtctagtca gagcctcctg catagtgatg gaaagaccta tttgtattgg    120
tacctgcaga agccaggcca gcctccacag ctcctgatct atgaagtttc caaccggttc    180
tctggagtgc cagataggtt cagtggcagc gggtcaggga cagatttcac actgaaaatc    240
agccgggtgg aggctgagga tgttggggtt tattactgca tgcaaagtat acagcttcct    300
cc                                                                   302
```

```
<210> SEQ ID NO 34
<211> LENGTH: 100
<212> TYPE: PRT
<213> ORGANISM: Artificial Sequence
<220> FEATURE:
<223> OTHER INFORMATION: Variable region of humanized light chain DPK12

<400> SEQUENCE: 34
```

```
Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
          100
```

```
<210> SEQ ID NO 35
<211> LENGTH: 345
<212> TYPE: DNA
<213> ORGANISM: Artificial Sequence
<220> FEATURE:
<223> OTHER INFORMATION: Variable region of humanized heavy chain HZI

<400> SEQUENCE: 35
```

```
caggtccagc tggtgcagtc tggagctgaa gtggtgaagc ctggggcctc agtgaaggtt    60
tcctgcaaag cttctggcta cgcattcagt agttcttgga tgaactgggt gcgacaggcc    120
cctggacagg gtcttgagtg gattggacgg atttatcctg agatggagaa tactaactac    180
gcacagaagt tccagggcaa ggccacactg actgcagaca aatccacgag cacagcctac    240
atggagctca gcagcctgag atctgaggac acggcggtct atttctgtgc aagagagtac    300
gacgaggctt actggggcca aggaactctg gtcactgtct cttca                    345
```

```
<210> SEQ ID NO 36
<211> LENGTH: 115
<212> TYPE: PRT
<213> ORGANISM: Artificial Sequence
<220> FEATURE:
<223> OTHER INFORMATION: Variable region of humanized heavy chain HZI

<400> SEQUENCE: 36
```

```
Gln Val Gln Leu Val Gln Ser Gly Ala Glu Val Val Lys Pro Gly Ala
 1               5                  10                  15

Ser Val Lys Val Ser Cys Lys Ala Ser Gly Tyr Ala Phe Ser Ser Ser
            20                  25                  30

Trp Met His Trp Val Arg Gln Ala Pro Gly Gln Gly Leu Glu Trp Ile
```

```
                    35                  40                  45
Gly Arg Ile Tyr Pro Gly Asp Gly Ser Thr Ser Tyr Ala Gln Lys Phe
        50                  55                  60
Gln Gly Lys Ala Thr Leu Thr Ala Asp Lys Ser Thr Ser Thr Ala Tyr
65                  70                  75                  80
Met Glu Leu Ser Ser Leu Arg Ser Glu Asp Thr Ala Val Tyr Phe Cys
                85                  90                  95
Ala Arg Glu Tyr Asp Glu Ala Tyr Trp Gly Gln Gly Thr Leu Val Thr
            100                 105                 110
Val Ser Ser
        115

<210> SEQ ID NO 37
<211> LENGTH: 336
<212> TYPE: DNA
<213> ORGANISM: Artificial Sequence
<220> FEATURE:
<223> OTHER INFORMATION: Variable region of humanized light chain HZI

<400> SEQUENCE: 37
gatatcttga tgacccaaac tccactttct tgtcggtta cccctggaca accagcctct     60
atctcttgca agtcaagtca gagcctctta tatagtaatg aaaaaccta tttgaattgg   120 ttattacaga agccaggcca gtctccaaag cgcctaatct atctggtgtc taaactggac   180
tctggagtcc ctgacaggtt cagtggcagt ggatcaggaa cagattttac actgaaaatc   240
agcagagtgg aggctgagga tgttggagtt tattactgcg tgcaaggtac acattttcct   300
cagacgttcg gtggaggcac caaggtggaa atcaaa                            336

<210> SEQ ID NO 38
<211> LENGTH: 112
<212> TYPE: PRT
<213> ORGANISM: Artificial Sequence
<220> FEATURE:
<223> OTHER INFORMATION: Variable region of humanized light chain HZI

<400> SEQUENCE: 38

Asp Ile Leu Met Thr Gln Thr Pro Leu Ser Leu Ser Val Thr Pro Gly
1               5                   10                  15
Gln Pro Ala Ser Ile Ser Cys Lys Ser Ser Gln Ser Leu Leu Tyr Ser
            20                  25                  30
Asn Gly Lys Thr Tyr Leu Tyr Trp Leu Leu Gln Lys Pro Gly Gln Ser
        35                  40                  45
Pro Lys Arg Leu Ile Tyr Leu Val Ser Lys Leu Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Val Gln Gly
                85                  90                  95
Thr His Phe Pro Gln Thr Phe Gly Gly Gly Thr Lys Val Glu Ile Lys
            100                 105                 110
```